US008435284B2

(12) United States Patent
Eidenschink et al.

(10) Patent No.: US 8,435,284 B2
(45) Date of Patent: May 7, 2013

(54) TELESCOPING BIFURCATED STENT

(75) Inventors: Tracee Eidenschink, Wayzata, MN (US); Michael P. Meyer, Richfield, MN (US); Matt Heidner, Maple Grove, MN (US); Daniel Gregorich, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1646 days.

(21) Appl. No.: 11/300,210

(22) Filed: Dec. 14, 2005

(65) Prior Publication Data
US 2007/0135904 A1 Jun. 14, 2007

(51) Int. Cl.
*A61F 2/06* (2006.01)

(52) U.S. Cl.
USPC .......... 623/1.35; 623/1.15; 623/1.11

(58) Field of Classification Search ........ 623/1.15, 623/1.16, 1.18, 1.19, 1.2, 1.35; 606/108
See application file for complete search history.

(56) References Cited

U.S. PATENT DOCUMENTS

| | | |
|---|---|---|
| 1,596,754 A | 8/1926 | Moschelle |
| 1,861,769 A | 6/1932 | Wappler |
| 2,845,959 A | 8/1958 | Sidebotham |
| 3,872,893 A | 3/1975 | Roberts .......... 138/121 |
| 4,309,994 A | 1/1982 | Grunwald .......... 128/214 R |
| 4,410,476 A | 10/1983 | Redding et al. .......... 264/173 |
| 4,413,989 A | 11/1983 | Schjeldahl et al. .......... 604/96 |
| 4,421,810 A | 12/1983 | Rasmussen .......... 428/109 |
| 4,454,887 A | 6/1984 | Kruger .......... 128/772 |
| 4,552,554 A | 11/1985 | Gould et al. .......... 604/51 |
| 4,681,570 A | 7/1987 | Dalton .......... 604/282 |
| 4,689,174 A | 8/1987 | Lupke .......... 156/470 |
| 4,730,616 A | 3/1988 | Frisbie et al. .......... 128/348.1 |
| 4,769,005 A | 9/1988 | Ginsburg et al. .......... 604/53 |
| 4,774,949 A | 10/1988 | Fogarty |
| 4,896,670 A | 1/1990 | Crittenden .......... 606/194 |
| 4,900,314 A | 2/1990 | Quackenbush .......... 604/282 |
| 4,905,667 A | 3/1990 | Foerster et al. .......... 128/4 |
| 4,957,508 A | 9/1990 | Kaneko et al. .......... 632/12 |
| 4,983,166 A | 1/1991 | Yamawaki .......... 604/96 |
| 4,994,071 A | 2/1991 | Gregor .......... 606/194 |
| 5,054,501 A | 10/1991 | Chuttani et al. .......... 128/772 |
| 5,122,125 A | 6/1992 | Deuss .......... 604/282 |
| 5,147,317 A | 9/1992 | Shank et al. .......... 604/164 |

(Continued)

FOREIGN PATENT DOCUMENTS

| | | |
|---|---|---|
| CA | 2220864 | 7/1999 |
| DE | 9014845 | 2/1991 |

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — Darwin Erezo
*Assistant Examiner* — Jing Ou
(74) *Attorney, Agent, or Firm* — Vidas, Arrett & Steinkraus, P.A.

(57) ABSTRACT

A bifurcated stent that uses telescoping rings to support or form the side branch lumen. This design allows the bifurcation branch to extend easily, to a useful distance, and to be deployed along oblique angles. Best of all, this design avoids the need to deploy a bent stent.

11 Claims, 15 Drawing Sheets

U.S. PATENT DOCUMENTS

| | | | | |
|---|---|---|---|---|
| 5,156,620 | A | 10/1992 | Pigott | 623/1 |
| 5,217,440 | A | 6/1993 | Frassica | 604/282 |
| 5,219,355 | A | 6/1993 | Parodi et al. | 606/191 |
| 5,244,619 | A | 9/1993 | Burnham | 264/173 |
| 5,320,605 | A | 6/1994 | Sahota | 604/101 |
| 5,337,733 | A | 8/1994 | Bauerfeind et al. | 128/4 |
| 5,342,387 | A | 8/1994 | Summers | 606/198 |
| 5,350,395 | A | 9/1994 | Yock | 606/194 |
| 5,387,235 | A | 2/1995 | Chuter | 623/1 |
| 5,404,887 | A | 4/1995 | Prather | 128/772 |
| 5,417,208 | A | 5/1995 | Winkler | 128/642 |
| 5,443,497 | A | 8/1995 | Venbrux | 623/1 |
| 5,445,624 | A | 8/1995 | Jimenez | 604/280 |
| 5,456,712 | A | 10/1995 | Maginot | 623/1 |
| 5,458,605 | A | 10/1995 | Klemm | 606/108 |
| 5,476,471 | A | 12/1995 | Shifrin et al. | 606/151 |
| 5,487,730 | A | 1/1996 | Marcadis et al. | 604/96 |
| 5,489,271 | A | 2/1996 | Andersen | 604/102 |
| 5,496,292 | A | 3/1996 | Burnham | 604/282 |
| 5,575,771 | A | 11/1996 | Walinsky | 604/96 |
| 5,578,074 | A | 11/1996 | Mirigian | 623/1 |
| 5,591,228 | A | 1/1997 | Edoga | 623/1 |
| 5,599,300 | A | 2/1997 | Weaver et al. | 604/54 |
| 5,607,444 | A | 3/1997 | Lam et al. | 606/194 |
| 5,609,605 | A | 3/1997 | Marshall et al. | 606/191 |
| 5,609,627 | A | 3/1997 | Goicoechea et al. | 623/1 |
| 5,613,980 | A | 3/1997 | Chauhan | 606/194 |
| 5,617,878 | A | 4/1997 | Taheri | 128/898 |
| 5,618,299 | A | 4/1997 | Khosravi et al. | 606/198 |
| 5,632,762 | A | 5/1997 | Myler | 606/194 |
| 5,632,763 | A | 5/1997 | Glastra | 606/194 |
| 5,632,772 | A | 5/1997 | Alcime et al. | 623/1 |
| 5,636,641 | A | 6/1997 | Fariabi | 600/585 |
| 5,639,278 | A | 6/1997 | Dereume et al. | 623/1 |
| 5,669,905 | A | 9/1997 | Scheldrup | 606/32 |
| 5,669,924 | A | 9/1997 | Shaknovich | 606/108 |
| 5,669,932 | A | 9/1997 | Fischell et al. | 606/198 |
| 5,672,153 | A | 9/1997 | Lax et al. | 604/22 |
| 5,676,697 | A | 10/1997 | McDonald | 623/1 |
| 5,683,450 | A | 11/1997 | Goicoechea et al. | 623/1 |
| 5,693,086 | A | 12/1997 | Goicoechea et al. | 623/1 |
| 5,697,971 | A | 12/1997 | Fischell et al. | 623/1 |
| 5,707,348 | A | 1/1998 | Krogh | 602/41 |
| 5,709,713 | A | 1/1998 | Evans et al. | 623/1 |
| 5,720,735 | A | 2/1998 | Dorros | 604/284 |
| 5,735,872 | A | 4/1998 | Carpenter et al. | 606/198 |
| 5,749,825 | A | 5/1998 | Fischell et al. | 600/3 |
| 5,749,890 | A | 5/1998 | Shaknovich | 606/198 |
| 5,755,734 | A | 5/1998 | Richter et al. | 606/194 |
| 5,755,735 | A | 5/1998 | Richter et al. | 606/194 |
| 5,755,770 | A | 5/1998 | Ravenscroft | 623/1 |
| 5,755,771 | A | 5/1998 | Penn et al. | 623/1 |
| 5,755,772 | A | 5/1998 | Evans et al. | 623/1 |
| 5,755,773 | A | 5/1998 | Evans et al. | 623/1 |
| 5,755,778 | A | 5/1998 | Kleshinski | 623/1 |
| 5,776,101 | A | 7/1998 | Goy | 604/104 |
| 5,782,906 | A | 7/1998 | Marshall et al. | 604/194 |
| 5,797,951 | A | 8/1998 | Mueller | |
| 5,800,508 | A | 9/1998 | Goicoechea et al. | 623/1 |
| 5,800,520 | A | 9/1998 | Fogarty et al. | 623/1 |
| 5,824,036 | A | 10/1998 | Lauterjung | 623/1 |
| 5,824,040 | A | 10/1998 | Cox et al. | 623/1 |
| 5,827,320 | A | 10/1998 | Richter et al. | 606/194 |
| 5,851,464 | A | 12/1998 | Davila et al. | 264/103 |
| 5,855,600 | A | 1/1999 | Alt | 623/1 |
| 5,868,777 | A | 2/1999 | Lam | 606/194 |
| 5,893,887 | A | 4/1999 | Jayaraman | 623/1 |
| 5,906,640 | A | 5/1999 | Penn et al. | 623/1 |
| 5,916,263 | A | 6/1999 | Goicoechea et al. | 623/1 |
| 5,921,995 | A | 7/1999 | Kleshinski | 606/153 |
| 5,938,696 | A | 8/1999 | Goicoechea et al. | 623/1 |
| 5,961,490 | A | 10/1999 | Adams | 604/96 |
| 5,961,548 | A | 10/1999 | Shmulewitz | 623/1 |
| 5,968,089 | A | 10/1999 | Krajicek | 623/1 |
| 5,972,017 | A | 10/1999 | Berg et al. | 606/198 |
| 5,984,929 | A | 11/1999 | Bashiri | 606/108 |
| 5,984,955 | A | 11/1999 | Wisselink | 623/1 |
| 5,993,481 | A | 11/1999 | Marcade et al. | 623/1 |
| 6,013,054 | A | 1/2000 | Jiun Yan | 604/96 |
| 6,013,091 | A | 1/2000 | Ley et al. | 83/150 |
| 6,016,810 | A | 1/2000 | Ravenscroft | 128/898 |
| 6,017,324 | A | 1/2000 | Tu et al. | 604/96 |
| 6,017,363 | A | 1/2000 | Hojeibane | 623/1 |
| 6,030,414 | A | 2/2000 | Taheri | 623/1 |
| 6,033,433 | A | 3/2000 | Her | 623/1 |
| 6,033,434 | A | 3/2000 | Borghi | 623/1 |
| 6,033,435 | A | 3/2000 | Penn et al. | 623/1 |
| 6,039,758 | A | 3/2000 | Quiachon et al. | 623/1 |
| 6,045,557 | A | 4/2000 | White et al. | 606/108 |
| 6,048,360 | A | 4/2000 | Khosravi et al. | 623/1 |
| 6,048,361 | A | 4/2000 | Von Gepen | 623/1 |
| 6,051,020 | A | 4/2000 | Goicoechea et al. | 623/1 |
| 6,056,722 | A | 5/2000 | Jayaraman | 604/102 |
| 6,056,775 | A | 5/2000 | Borghi et al. | 623/1.16 |
| 6,059,824 | A | 5/2000 | Taheri | 623/1 |
| 6,068,655 | A | 5/2000 | Seguin et al. | 623/1 |
| 6,071,298 | A | 6/2000 | Lashinski et al. | 606/198 |
| 6,086,611 | A | 7/2000 | Duffy et al. | 623/1 |
| 6,090,133 | A | 7/2000 | Richter et al. | 623/1 |
| 6,093,203 | A | 7/2000 | Uflacker | 612/1.12 |
| 6,096,073 | A | 8/2000 | Webster et al. | 623/1.16 |
| 6,099,497 | A | 8/2000 | Adams et al. | 604/96.01 |
| 6,099,558 | A | 8/2000 | White | 623/1.16 |
| 6,099,560 | A | 8/2000 | Penn et al. | 623/1.35 |
| 6,102,938 | A | 8/2000 | Evans et al. | 623/1 |
| 6,113,579 | A | 9/2000 | Eidenschink | 604/264 |
| 6,117,117 | A | 9/2000 | Mauch | 604/284 |
| 6,117,156 | A | 9/2000 | Richter et al. | 606/194 |
| 6,129,738 | A | 10/2000 | Lashinski et al. | 606/194 |
| 6,129,754 | A | 10/2000 | Kanesaka | 623/1 |
| 6,132,459 | A | 10/2000 | Piplani et al. | 623/1.13 |
| 6,142,973 | A | 11/2000 | Carleton et al. | 604/96 |
| 6,143,002 | A | 11/2000 | Vietmeier | 606/108 |
| 6,159,238 | A | 12/2000 | Killion et al. | 623/1.11 |
| 6,165,195 | A | 12/2000 | Wilson et al. | 606/194 |
| 6,165,213 | A | 12/2000 | Goicoechea et al. | 623/1.34 |
| 6,168,621 | B1 | 1/2001 | Vrba | 623/1.2 |
| 6,183,509 | B1 | 2/2001 | Dibie | 623/1.35 |
| 6,197,046 | B1 | 3/2001 | Piplani et al. | 623/1.11 |
| 6,197,049 | B1 | 3/2001 | Shaolian et al. | 623/1.35 |
| 6,203,568 | B1 | 3/2001 | Lombardi et al. | 623/1.13 |
| 6,210,380 | B1 | 4/2001 | Mauch | 604/284 |
| 6,210,429 | B1 | 4/2001 | Vardi | 623/1.11 |
| 6,210,431 | B1 | 4/2001 | Power | 623/1.11 |
| 6,210,433 | B1 | 4/2001 | Larre | 623/1.15 |
| 6,217,527 | B1 | 4/2001 | Selmon et al. | 600/285 |
| 6,221,080 | B1 | 4/2001 | Power | 606/108 |
| 6,221,090 | B1 | 4/2001 | Wilson | 606/194 |
| 6,221,098 | B1 | 4/2001 | Wilson et al. | 623/1.11 |
| 6,231,563 | B1 | 5/2001 | White et al. | 604/523 |
| 6,231,598 | B1 | 5/2001 | Berry et al. | |
| 6,238,430 | B1 | 5/2001 | Klumb et al. | 623/1.11 |
| 6,248,122 | B1 | 6/2001 | Klumb et al. | 606/194 |
| 6,251,133 | B1 | 6/2001 | Richter et al. | 623/1.16 |
| 6,254,593 | B1 | 7/2001 | Wilson | 606/1.11 |
| 6,258,073 | B1 | 7/2001 | Mauch | 604/284 |
| 6,258,115 | B1 | 7/2001 | Dubrul | 606/200 |
| 6,258,116 | B1 | 7/2001 | Hojeibane | 623/1.16 |
| 6,261,273 | B1 | 7/2001 | Ruiz | 604/284 |
| 6,261,305 | B1 | 7/2001 | Marotta et al. | 606/200 |
| 6,261,316 | B1 | 7/2001 | Shaolian et al. | 623/1.11 |
| 6,264,662 | B1 | 7/2001 | Lauterjung | 606/108 |
| 6,264,686 | B1 | 7/2001 | Rieu et al. | 623/1.16 |
| 6,273,909 | B1 | 8/2001 | Kugler et al. | 623/1.13 |
| 6,287,277 | B1 | 9/2001 | Yan | 604/96.01 |
| 6,290,673 | B1 | 9/2001 | Shanley | 604/102.02 |
| 6,293,968 | B1 | 9/2001 | Taheri | 623/1.15 |
| 6,302,906 | B1 | 10/2001 | Goicoechea et al. | 623/1.11 |
| 6,302,908 | B1 | 10/2001 | Parodi | 623/1.31 |
| 6,306,164 | B1 | 10/2001 | Kujawski | 623/1.25 |
| 6,312,461 | B1 | 11/2001 | Unsworth et al. | 623/1.19 |
| 6,319,278 | B1 | 11/2001 | Quinn et al. | 623/1.13 |
| 6,322,587 | B1 | 11/2001 | Quiachon et al. | 623/1.23 |
| 6,325,819 | B1 | 12/2001 | Pavcnik et al. | 623/1.11 |
| 6,325,822 | B1 | 12/2001 | Chouinard et al. | 623/1.15 |
| 6,325,826 | B1 | 12/2001 | Vardi | 623/1.35 |
| 6,334,864 | B1 | 1/2002 | Amplatz et al. | 606/200 |

| | | | | | | |
|---|---|---|---|---|---|---|
| 6,334,870 B1 | 1/2002 | Ehr .................................. 623/1.16 | | 2002/0156517 A1 | 10/2002 | Perouse ......................... 623/1.11 |
| 6,346,089 B1 | 2/2002 | Dibie ............................... 623/1.15 | | 2002/0165604 A1 | 11/2002 | Shanley ......................... 623/1.15 |
| 6,355,060 B1 | 3/2002 | Lenker et al. ................... 623/1.34 | | 2002/0173835 A1 | 11/2002 | Bourang et al. ............... 623/1.11 |
| 6,361,544 B1 | 3/2002 | Wilson et al. ................... 606/194 | | 2002/0173840 A1 | 11/2002 | Brucker et al. ................ 623/1.16 |
| 6,361,555 B1 | 3/2002 | Wilson ............................ 623/1.11 | | 2002/0183763 A1 | 12/2002 | Callol et al. ................... 606/108 |
| 6,383,213 B2 | 5/2002 | Wilson et al. ................... 623/1.11 | | 2002/0193872 A1 | 12/2002 | Trout, III et al. .............. 623/1.34 |
| 6,387,120 B2 | 5/2002 | Wilson et al. ................... 623/1.11 | | 2002/0193873 A1 | 12/2002 | Brucker .......................... 623/1.11 |
| 6,395,018 B1 | 5/2002 | Castaneda ....................... 623/1.13 | | 2003/0009209 A1 | 1/2003 | Hojeibane ...................... 623/1.11 |
| 6,436,104 B2 | 8/2002 | Hojeibane ...................... 606/108 | | 2003/0028233 A1 | 2/2003 | Vardi et al. .................... 623/1.11 |
| 6,436,134 B2 | 8/2002 | Richter ........................... 623/1.15 | | 2003/0050688 A1 | 3/2003 | Fischell et al. ................ 623/1.15 |
| 6,468,301 B1 | 10/2002 | Amplatz et al. ................ 623/1.13 | | 2003/0055378 A1 | 3/2003 | Wang et al. .................. 604/103.07 |
| 6,508,836 B2 | 1/2003 | Wilson et al. ................... 623/1.35 | | 2003/0055483 A1 | 3/2003 | Gumm ........................... 623/1.11 |
| 6,514,228 B1 | 2/2003 | Hamilton ....................... 604/96.01 | | 2003/0074047 A1 | 4/2003 | Richter .......................... 623/1.11 |
| 6,517,515 B1 | 2/2003 | Eidenschink .................. 604/101.05 | | 2003/0093109 A1 | 5/2003 | Mauch ........................... 606/194 |
| 6,517,558 B2 | 2/2003 | Gittings et al. ................. 606/153 | | 2003/0097169 A1 | 5/2003 | Brucker et al. ................ 623/1.11 |
| 6,520,988 B1 | 2/2003 | Colombo et al. ............... 623/1.35 | | 2003/0114912 A1 | 6/2003 | Sequin et al. .................. 623/1.11 |
| 6,537,284 B1 | 3/2003 | Priddy ............................ 606/108 | | 2003/0125791 A1 | 7/2003 | Sequin et al. .................. 623/1.11 |
| 6,540,779 B2 | 4/2003 | Richter et al. .................. 623/1.35 | | 2003/0125802 A1 | 7/2003 | Callol et al. ................... 623/1.35 |
| 6,579,308 B1 | 6/2003 | Jansen ............................ 623/1.12 | | 2003/0135259 A1 | 7/2003 | Simso ............................ 623/1.12 |
| 6,579,309 B1 | 6/2003 | Loos .............................. 623/1.16 | | 2003/0181923 A1 | 9/2003 | Vardi ............................. 606/108 |
| 6,579,312 B2 | 6/2003 | Wilson et al. ................... 623/1.35 | | 2003/0195606 A1 | 10/2003 | Davidson ...................... 623/1.15 |
| 6,582,394 B1 | 6/2003 | Reiss .............................. 604/96 | | 2004/0006381 A1 | 1/2004 | Sequin et al. .................. 623/1.12 |
| 6,596,020 B2 | 7/2003 | Vardi et al. ..................... 623/1.11 | | 2004/0015227 A1 | 1/2004 | Vardi et al. .................... 623/1.16 |
| 6,599,315 B2 | 7/2003 | Wilson ............................ 623/1.11 | | 2004/0044396 A1 | 3/2004 | Clerc et al. .................... 623/1.13 |
| 6,599,316 B2 | 7/2003 | Vardi .............................. 623/1.11 | | 2004/0059406 A1 | 3/2004 | Cully et al. .................... 623/1.11 |
| 6,645,242 B1 | 11/2003 | Quinn ............................ 623/1.16 | | 2004/0088007 A1 | 5/2004 | Eidenschink .................. 607/1 |
| 6,689,156 B1 | 2/2004 | Davidson et al. .............. 623/1.11 | | 2004/0117003 A1 | 6/2004 | Ouriel et al. ................... 623/1.35 |
| 6,692,483 B2 | 2/2004 | Vardi et al. ..................... 604/529 | | 2004/0133268 A1 | 7/2004 | Davidson et al. .............. 623/1.35 |
| 6,694,877 B1 | 2/2004 | Brucker .......................... 623/1.16 | | 2004/0138732 A1 | 7/2004 | Suhr et al. ...................... 623/1.11 |
| 6,695,877 B2 | 2/2004 | Brucker et al. ................. 623/1.16 | | 2004/0138737 A1 | 7/2004 | Davidson ...................... 623/1.15 |
| 6,706,062 B2 | 3/2004 | Vardi et al. ..................... 623/1.15 | | 2004/0148006 A1 | 7/2004 | Davidson et al. .............. 623/1.11 |
| 6,749,628 B1 | 6/2004 | Callol et al. .................... 623/1.15 | | 2004/0172121 A1 | 9/2004 | Eidenschink et al. ......... 623/1.11 |
| 6,776,793 B2 | 8/2004 | Brown et al. ................... 623/1.15 | | 2004/0186560 A1 | 9/2004 | Alt ................................. 623/1.35 |
| 6,811,566 B1 | 11/2004 | Penn et al. ...................... 623/1.15 | | 2004/0225345 A1 | 11/2004 | Fischell et al. ................ 623/1.11 |
| 6,835,203 B1 | 12/2004 | Vardi .............................. 623/1.16 | | 2004/0267352 A1 | 12/2004 | Davidson et al. .............. 623/1.16 |
| 6,858,038 B2 | 2/2005 | Heuser ........................... 623/1.35 | | 2005/0004656 A1 | 1/2005 | Das ................................ 623/1.16 |
| 6,884,258 B2 | 4/2005 | Vardi et al. ..................... 623/1.11 | | 2005/0010278 A1 | 1/2005 | Vardi ............................. 623/1.16 |
| 6,896,699 B2 | 5/2005 | Wilson et al. ................... 623/1.35 | | 2005/0015108 A1 | 1/2005 | Williams et al. ............... 606/194 |
| 6,932,837 B2 | 8/2005 | Amplatz et al. ................ 623/1.15 | | 2005/0015135 A1 | 1/2005 | Shanley ......................... 623/1.11 |
| 6,955,687 B2 | 10/2005 | Richter et al. .................. 623/1.35 | | 2005/0060027 A1 | 3/2005 | Khenansho et al. ........... 623/1.35 |
| 6,955,688 B2 | 10/2005 | Wilson et al. ................... 623/1.35 | | 2005/0096726 A1 | 5/2005 | Sequin et al. .................. 623/1.12 |
| 6,962,602 B2 | 11/2005 | Vardi et al. ..................... 623/1.11 | | 2005/0102021 A1 | 5/2005 | Osborne ........................ 623/1.13 |
| 7,018,400 B2 | 3/2006 | Lashinski et al. .............. 623/1.11 | | 2005/0102023 A1 | 5/2005 | Yadin ............................. 623/1.16 |
| 7,056,323 B2 | 6/2006 | Mareiro et al. ................. 606/108 | | 2005/0119731 A1 | 6/2005 | Brucker et al. ................ 623/1.35 |
| 7,060,091 B2 | 6/2006 | Killion et al. .................. 623/1.15 | | 2005/0125076 A1 | 6/2005 | Ginn .............................. 623/23.65 |
| 2001/0002443 A1 | 5/2001 | Parodi | | 2005/0131526 A1 | 6/2005 | Wong |
| 2001/0002927 A1 | 6/2001 | Detampel | | 2005/0149161 A1 | 7/2005 | Eidenschink et al. ......... 623/1.11 |
| 2001/0002943 A1 | 6/2001 | Nagayama et al. | | 2005/0154442 A1 | 7/2005 | Eidenschink et al. ......... 623/1.11 |
| 2001/0003161 A1 | 6/2001 | Vardi et al. | | 2005/0154444 A1 | 7/2005 | Quadri ........................... 623/1.16 |
| 2001/0004705 A1 | 6/2001 | Killion et al. | | 2005/0183259 A1 | 8/2005 | Eidenschink et al. ......... 29/508 |
| 2001/0004706 A1 | 6/2001 | Hojeibane | | 2005/0209673 A1 | 9/2005 | Shaked .......................... 623/1.11 |
| 2001/0004707 A1 | 6/2001 | Dereume et al. | | 2005/0228483 A1 | 10/2005 | Kaplan .......................... 623/1.11 |
| 2001/0004823 A1 | 6/2001 | Cronin et al. | | 2006/0036315 A1 | 2/2006 | Yadin et al. .................... 623/1.35 |
| 2001/0007954 A1 | 7/2001 | Shaolian et al. | | 2006/0041303 A1 | 2/2006 | Israel ............................. 623/1.11 |
| 2001/0012927 A1 | 8/2001 | Mauch ........................... 604/284 | | 2006/0079956 A1 | 4/2006 | Eigler et al. ................... 623/1.35 |
| 2001/0016766 A1 | 8/2001 | Vardi et al. | | 2006/0173528 A1 | 8/2006 | Feld et al. ...................... 623/1.15 |
| 2001/0016767 A1 | 8/2001 | Wilson et al. | | 2007/0073376 A1 | 3/2007 | Krolik et al. .................. 623/1.11 |
| 2001/0016768 A1 | 8/2001 | Wilson et al. | | | | |
| 2001/0020173 A1 | 9/2001 | Klumb et al. | | FOREIGN PATENT DOCUMENTS | | |
| 2001/0020184 A1 | 9/2001 | Dehdashtian et al. | | | | |
| 2001/0025195 A1 | 9/2001 | Shaolian et al. | | DE | 29701758 | 3/1997 |
| 2001/0027291 A1 | 10/2001 | Shanley | | DE | 29708803 | 7/1997 |
| 2001/0027338 A1 | 10/2001 | Greenberg ..................... 623/1.13 | | EP | 0347023 | 12/1989 |
| 2001/0029396 A1 | 10/2001 | Wilson et al. | | EP | 0479730 | 4/1992 |
| 2001/0037116 A1 | 11/2001 | Wilson et al. ................... 606/108 | | EP | 0647148 | 4/1995 |
| 2001/0037138 A1 | 11/2001 | Wilson et al. ................... 623/1.11 | | EP | 0686379 | 12/1995 |
| 2001/0039448 A1 | 11/2001 | Dibie ............................... 623/1.16 | | EP | 0804907 | 11/1997 |
| 2001/0049552 A1 | 12/2001 | Richter et al. .................. 623/1.15 | | EP | 0751752 | 6/1998 |
| 2001/0056297 A1 | 12/2001 | Hojeibane ...................... 623/1.16 | | EP | 0479557 | 7/1998 |
| 2002/0013618 A1 | 1/2002 | Marotta et al. ................. 623/1.15 | | EP | 0876805 | 11/1998 |
| 2002/0013619 A1 | 1/2002 | Shanley ......................... 623/1.15 | | EP | 0880949 | 12/1998 |
| 2002/0022874 A1 | 2/2002 | Wilson ............................ 623/1.15 | | EP | 0891751 | 1/1999 |
| 2002/0026232 A1 | 2/2002 | Marotta et al. ................. 623/1.16 | | EP | 0895759 | 2/1999 |
| 2002/0035392 A1 | 3/2002 | Wilson ............................ 623/1.11 | | EP | 0904745 | 3/1999 |
| 2002/0042650 A1 | 4/2002 | Vardi et al. ..................... 623/1.35 | | EP | 0937442 | 8/1999 |
| 2002/0052648 A1 | 5/2002 | McGuckin, Jr. et al. ..... 623/1.35 | | EP | 0783873 | 4/2000 |
| 2002/0072790 A1 | 6/2002 | McGuckin, Jr. et al. ..... 623/1.12 | | EP | 1031328 | 8/2000 |
| 2002/0111675 A1 | 8/2002 | Wilson ............................ 715/530 | | EP | 1031329 | 8/2000 |
| 2002/0156516 A1 | 10/2002 | Vardi et al. ..................... 623/1.11 | | EP | 0883384 | 12/2000 |
| | | | | EP | 0862392 | 8/2001 |

| | | |
|---|---|---|
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 4/1997 |
| FR | 2756173 | 5/1998 |
| FR | 2760351 | 9/1998 |
| GB | 2337002 | 11/1999 |
| WO | 88/06026 | 8/1988 |
| WO | 92/19308 | 11/1992 |
| WO | 9521592 | 8/1995 |
| WO | 96/29955 | 10/1996 |
| WO | 9634580 | 11/1996 |
| WO | 9641592 | 12/1996 |
| WO | 9707752 | 3/1997 |
| WO | 9715346 | 5/1997 |
| WO | 9716217 | 5/1997 |
| WO | 97/26936 | 7/1997 |
| WO | 9741803 | 11/1997 |
| WO | 97/45073 | 12/1997 |
| WO | 9746174 | 12/1997 |
| WO | 9819628 | 5/1998 |
| WO | 98/31306 | 7/1998 |
| WO | 9836709 | 8/1998 |
| WO | 9837833 | 9/1998 |
| WO | 9847446 | 10/1998 |
| WO | 9847447 | 10/1998 |
| WO | 9848879 | 11/1998 |
| WO | 9853759 | 12/1998 |
| WO | 9903426 | 1/1999 |
| WO | 9904726 | 2/1999 |
| WO | 9913808 | 3/1999 |
| WO | 99/15103 | 4/1999 |
| WO | 9915108 | 4/1999 |
| WO | 9915109 | 4/1999 |
| WO | 9924104 | 5/1999 |
| WO | 9934749 | 7/1999 |
| WO | 9936002 | 7/1999 |
| WO | 9936015 | 7/1999 |
| WO | 9944539 | 9/1999 |
| WO | 9956661 | 11/1999 |
| WO | 9965419 | 12/1999 |
| WO | 0007523 | 2/2000 |
| WO | 0010485 | 3/2000 |
| WO | 0010489 | 3/2000 |
| WO | 0013613 | 3/2000 |
| WO | 0016719 | 3/2000 |
| WO | 0027307 | 5/2000 |
| WO | 0027463 | 5/2000 |
| WO | 0028922 | 5/2000 |
| WO | 0032266 | 6/2000 |
| WO | 0145594 | 6/2000 |
| WO | 0044307 | 8/2000 |
| WO | 0044309 | 8/2000 |
| WO | 0047134 | 8/2000 |
| WO | 0048531 | 8/2000 |
| WO | 0049951 | 8/2000 |
| WO | 0051523 | 9/2000 |
| WO | 0057813 | 10/2000 |
| WO | 00/71054 | 11/2000 |
| WO | 0067673 | 11/2000 |
| WO | 0071055 | 11/2000 |
| WO | 0074595 | 12/2000 |
| WO | 0121095 | 3/2001 |
| WO | 0121109 | 3/2001 |
| WO | 01021244 | 3/2001 |
| WO | 0130433 | 5/2001 |
| WO | 0135715 | 5/2001 |
| WO | 0135863 | 5/2001 |
| WO | 0139697 | 6/2001 |
| WO | 0139699 | 6/2001 |
| WO | 0141677 | 6/2001 |
| WO | 0143665 | 6/2001 |
| WO | 0143809 | 6/2001 |
| WO | 0145785 | 6/2001 |
| WO | 0149342 | 7/2001 |
| WO | 0154621 | 8/2001 |
| WO | 0154622 | 8/2001 |
| WO | 0158385 | 8/2001 |
| WO | 0160284 | 8/2001 |
| WO | 0170294 | 9/2001 |
| WO | 0170299 | 9/2001 |
| WO | 0174273 | 10/2001 |
| WO | 0189409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).
Caputo, Ronald P., "Stent Jail: A Minimum-Security Prison," *The American Journal of Cardiology*, vol. 77, pp. 1226-1230 (Jun. 1, 1996).
Colombo, M.D., Antonio, ""Kissing" Stent for Bifurcational Coronary Lesion," *Catheterization and Cardiovascular Diagnosis*, vol. 30, pp. 327-330 (Dec. 1993).
Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).
Katoh, M.D., Osamu, "New Double Wire Technique to Stent Ostial Lesions," *Catheterization and Cardiovascular Diagnosis*, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).
Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).
Satler, M.D., Lowell F., "Bifurcation Disease: To Treat or Not to Treat," *Catheterization and Cardiovascular Interventions*, vol. 50, pp. 411-412 (2000).
U.S. Appl. No. 9/325,996, filed Jun. 4, 1999, Vardi et al.
U.S. Appl. No. 9/614,472, filed Jul. 11, 2000, Davidson et al.
U.S. Appl. No. 9/663,111, filed Sep. 15, 2000, Davidson et al.
TRIO™ 14 PTCA Catheter, Re-engineering Over the Wire Balloon Technology, Company Brochure Copyright 1994.

TELESCOPING BIFURCATED STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

All U.S. patents and applications and all other published documents mentioned anywhere in this application are incorporated herein by reference in their entirety.

BRIEF SUMMARY OF THE INVENTION

This invention contemplates a number of embodiments where any one, any combination of some, or all of the embodiments can be incorporated into a stent and/or a stent delivery system and/or a method of use. In the context of these embodiments, the term telescoping means to extend away from a stent wall in a direction different from that of the longitudinal axis of a stent. Telescoping includes but is not limited each or any combination of: extending along a linear, varied, or curved path; extending at an oblique angle from the longitudinal axis of the stent; as well as extending along a path parallel to the longitudinal axis of the stent.

At least one embodiment of the invention is directed to a bifurcated stent being expandable from an unexpanded state to an expanded state, with a diameter smaller in the unexpanded state having a substantially tubular primary body defining a primary circumferential plane, a primary outer surface, a primary lumen and having a primary longitudinal axis extending therethrough; and a side branch assembly engaged to the primary body having at least one ring member, which is positioned substantially within the primary circumferential plane in the unexpanded state and defining a secondary circumferential plane, a secondary lumen, and having a secondary longitudinal axis extending therethrough, in the expanded state. The secondary lumen is in fluid communication with the primary lumen and forms an oblique angle with the primary longitudinal axis.

At least one embodiment of the invention is directed to a stent containing a bifurcation branch formed out of at least one ring connected to the stent. When deployed, this stent bridges vessel bifurcations by telescoping and aligning at least one ring into the vessel bifurcation. This bifurcation branch is an additional stent channel forking away from the first channel defined by the main body of the stent. The bifurcation branch is in fluid communication with the first channel and is formed by one or more rings in fluid communication with the main stent body. The rings are connected to the stent and (if there is more than one ring) to each other by connectors. In some embodiments, a telescoping ring bifurcation branch is configured to extend farther than a petal shaped stent bifurcation branch.

At least one embodiment of the invention is directed to a stent containing a bifurcation branch of two or more interconnected rings in fluid communication with the main stent body in which at least one ring is in an unextended state when the branch is not telescoped. When the branch is telescoped, the unextended ring(s) assume an extended state.

At least one embodiment of the invention is directed to a bifurcation branch of one or more rings in fluid communication with the main stent body in which the ring-ring or ring-stent connectors have a first length when the branch is untelescoped and a second length when the stent is telescoped. These different connector lengths allow for the rings to have a low profile when untelescoped and to allow for the rings to form a bifurcation branch of a large length when telescoped. This embodiment encompasses but is not limited to any stent connector known to people of ordinary skill in the art which has a longer length when expanded than when unexpanded.

At least one embodiment of the invention is directed to a bifurcation branch of one or more rings in fluid communication with the main stent body in which the ring-ring or ring-stent connectors have a bent structure when untelescoped that substantially straightens when telescoped.

At least one embodiment of the invention is directed to a bifurcation branch of one or more rings in fluid communication with the main stent body in which a ring-ring or ring-stent connectors is a flexible sinusoidal connector At least one embodiment of the invention is directed to a bifurcation branch of one or more rings in fluid communication with the main stent body in which a ring-ring or ring-stent connector is a pivot mechanism whose rotational motion changes the distance spanned by the connector.

At least one embodiment of the invention is directed to a bifurcation branch of one or more rings in fluid communication with the main stent body in which a ring-ring or ring-stent connector is a spring whose extension changes the distance spanned by the connector.

At least one embodiment of the invention is directed to a stent containing a bifurcation branch of two or more interconnected rings where when the branch is untelescoped, the rings are in an unexpanded state and are positioned concentrically adjacent to each other within or adjacent to the circumferential plane of the ring directly connected to the main stent body.

At least one embodiment of the invention is directed to a stent containing a bifurcation branch of at least one ring which has the configuration of an at least a partially self overlapping loop when unextended and contains a self extending mechanism. This mechanism expands the rings by removing the loop overlap when forming a stent bifurcation branch.

At least one embodiment of the invention is directed to a stent with a ring bifurcation branch containing a current detachment mechanism. In this embodiment, a locking mechanism restrains the telescoping and/or the ring extension from expanding until an electrical current is applied. Once applied, the current causes the mechanism to detach from the rings allowing the rings to expand and/or to telescope and form a bifurcation branch.

At least one embodiment of the invention is directed to a stent with a ring bifurcation branch in which a ring may extend until either a pre-defined circumference is reached or until the extension is blocked by an anatomical feature.

At least one embodiment of the invention is directed to a stent with a ring bifurcation branch in which a ring contains a ratchet configuration which allows it to either increase or decrease its circumference by moving a locking mechanism along a ring's perimeter in one direction. Because the ratchet configuration prevents the locking mechanism from moving in the reverse direction, it prevents any change in circumference size in the opposite direction.

At least one embodiment of the invention is directed to a stent with a ring bifurcation branch in which a ring or connector is made out of metal(s), polymer(s), and/or combinations thereof.

At least one embodiment of the invention is directed to a stent with a ring bifurcation branch in which the ring bifurcation is fed into the side body vessel by a support wire.

At least one embodiment of the invention is directed to a stent with a ring bifurcation branch in which when the final shape of the bifurcation branch is assumed, the branch is locked into place with a single or multiple tongue and grove latch mechanism.

At least one embodiment of the invention is directed to a stent with a ring bifurcation branch in which the branch is formed before the stent is expanded.

At least one embodiment of the invention is directed to a stent with a ring bifurcation branch in which the branch is formed after the stent is expanded.

At least one embodiment of the invention is directed to a stent with a ring bifurcation branch in which the branch is formed at substantially the same time that the stent is expanded.

This invention also encompasses embodiments where at least one ring member has an unexpanded circumference in the unexpanded state and an expanded circumference in the expanded state, wherein the expanded circumference is greater than the unexpanded circumference, where adjacent ring members are engaged one to the other by at least one connector, and where at least one connector has a first end, a second end and a length therebetween, each end being flexibly engaged to one of the rings.

This invention also encompasses embodiments where in the unexpanded state the plurality of rings are concentrically arranged relative to one another, where in the unexpanded state the ring members are positioned laterally adjacent to one another, where at least one of the expanded state and the unexpanded state at least two ring members have differing circumferences, and where the secondary lumen comprises a length and a diameter, the diameter tapering along at least a portion of the length.

This invention also encompasses embodiments where at least one connector comprises a polymeric sheath, where the polymeric sheath is at least partially constructed out of PTFE, where at least one ring member comprises a ratchet mechanism, in the expanded state the ratchet mechanism preventing the expanded circumference from reverting to a circumference smaller than the expanded circumference, where at least one ring member is constructed and arrange to self expand from the unexpanded circumference to the expanded circumference, where at least one ring member is engaged to the primary body by at least one engagement region, the at least one engagement region having an engaged state and a released state, in the engaged state the at least one ring member being retained in the unexpanded state and in the released state the at least one ring member being released to expand to the expanded state.

At least one embodiment of the invention is directed to a stent delivery system having an unexpanded state and an expanded state, a catheter having an elongated shaft connected to a distal end; and a stent, the stent having a generally tubular main body, the main body having a diameter, the main body defining an interior, a side branch opening, and a side branch assembly adjacent to the side branch opening, the side branch assembly comprising at least one ring, there being a distance between the main body and the at least one ring, in the unexpanded state the diameter of the main body being less than the diameter of the main body in the expanded state, in the unexpanded state the distance being less than the distance in the expanded state; wherein the in the unexpanded state, the stent is disposed the distal end of the catheter.

BRIEF DESCRIPTION OF THE SEVERAL VIEWS OF THE DRAWINGS

The invention is best understood from the following detailed description when read in connection with accompanying drawings, in which.

DETAILED DESCRIPTION OF THE INVENTION

Figure 1:
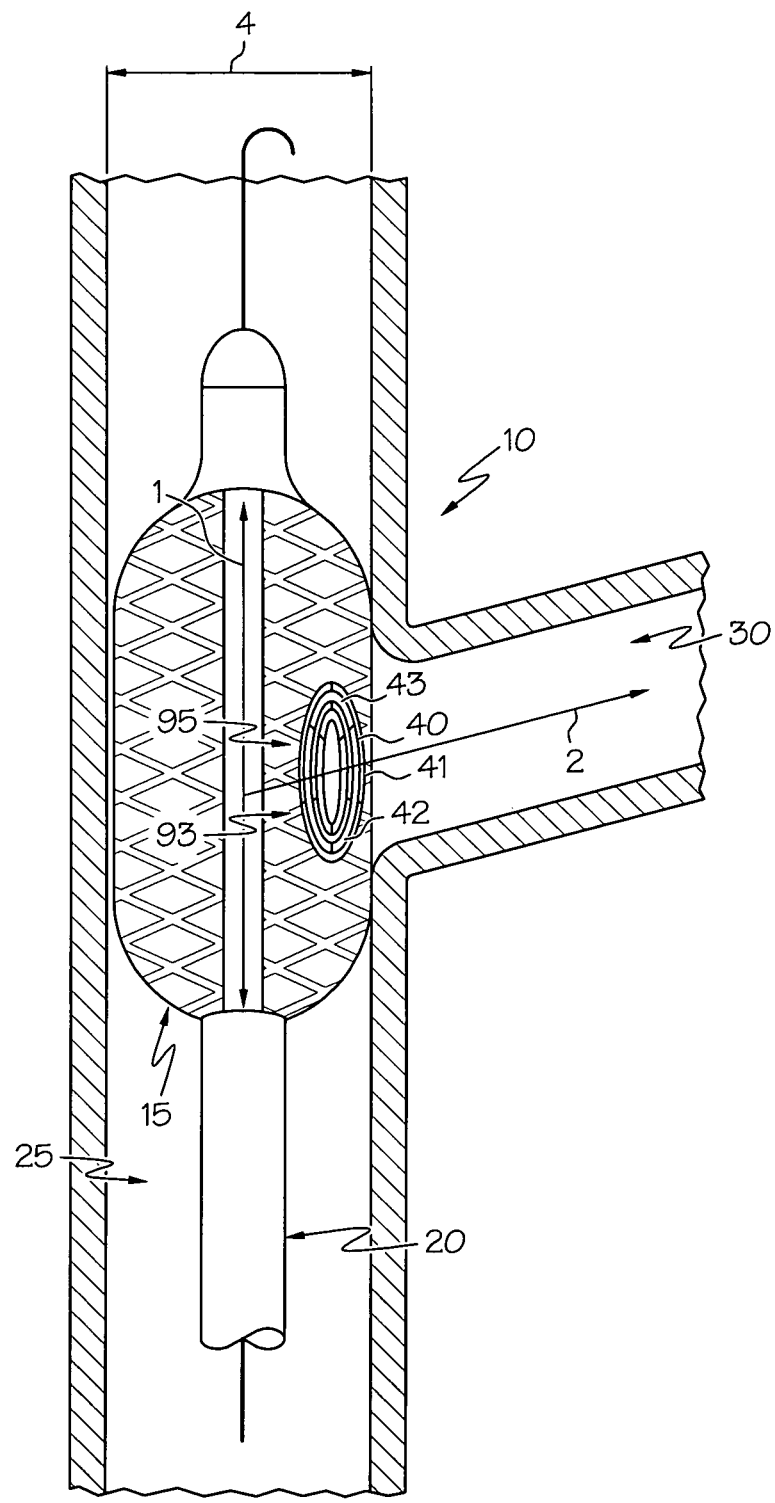
FIG. 1 is an image of an unexpanded stent containing an unextended ring type telescoping bifurcation branch.

The invention will next be illustrated with reference to the figures wherein the same numbers indicate similar elements in all figures. Such figures are intended to be illustrative rather than limiting and are included herewith to facilitate the explanation of the apparatus of the present invention.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Referring now to FIG. 1 there is shown an embodiment of the invention featuring an undeployed substantially tubular stent 10 in an unexpanded state placed on a catheter shaft 20 positioned within a body vessel, the body vessel having a first vessel lumen 25 and a second vessel lumen 30 which forms bifurcation from the first vessel lumen 25. The stent 10 deployed within the first vessel lumen 25 and is oriented along a primary longitudinal axis 1 which is forms an angle oblique to the secondary longitudinal axis 2 running along the length of the second vessel lumen 30. Positioned adjacent to the second vessel lumen 30 is a ring type side branch assembly 40 engaged to the primary stent body 15 by at least one connector 42 at an engagement region 93. The surface of the primary stent body defines a primary circumferential plane 95. In the unexpanded state, the side branch assembly 40 is positioned substantially along the primary circumferential plane 95. For the purposes of this application, the term "oblique" refers to an angle of greater than zero degrees, such as an angle of between about 1 and about 180 degrees. An oblique angle explicitly includes angles of about 90 degrees.

Side branch assembly 40 in FIG. 1 features a number of unextended rings or ring members 41 connected by inter-ring connectors 43. Although this drawing shows five interconnected concentric ring members 41, this invention is not limited to this number or configurations and encompasses any similar device with one or more ring members 41. In one possible embodiment, the unextended ring members 41 can have dissimilar circumferences and/or can fit into each other in a concentric "target" like configuration. This invention is not limited to a concentric arrangement of the ring members and encompasses any and all possible configurations known to people of ordinary skill in the art including stacked ring members and overlapping "olympic" ring arrangements. This invention also contemplates ring members that have the same or different circumferences when in the unextended state.

Figure 19:
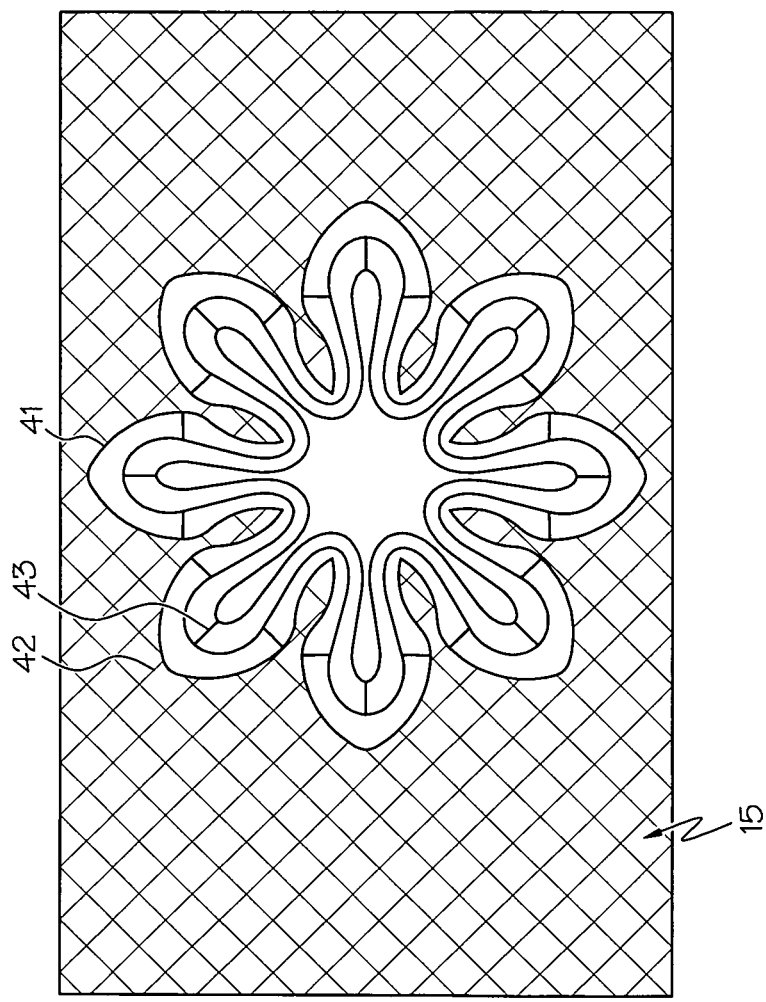
FIG. 19 is a close up view of an unextended ring type telescoping bifurcation branch in which the rings have a cloverleaf shape.

Although FIG. 1 illustrates the rings as having a generally oval or circular shape, this invention encompasses possible embodiments in which at least one ring of the side branch assembly has a non-oval or non-circular shape. Some other possible shapes for the rings include but are not limited to ellipse, cloverleaf (as illustrated in FIG. 19), and angular. In addition any given ring need not have a uniform or symmetrical shape and can have an irregular region. Rings of different shapes or sizes can be combined to form the side branch assembly.

This invention encompasses a number of mechanisms for extending the ring members 41. One mechanism involves constructing the ring members to be biased towards naturally extending and then blocking this extension with a releasable restraint. One mechanism for releasing the restraint is by locating the restraint at the engagement region 93 and connecting it to a current detachment mechanism which will release the restraint when an electrical current is received. Similarly the side branch assembly 40 can also be constructed biased to telescope naturally and be held back by a releasable restraint.

One method of releasing a biased stent 10 and/or side branch assembly 40 is to remove a restraining sheath from the stent when ready for deployment. Another method is to use a current detachment mechanism that will release a restraint and allow the ring members 41 to extend upon the receipt of an electrical current which degrades the integrity of a portion of the restraint. Current detachment mechanisms which are suitable for use in the present application may be similar to such mechanism that are known to be used in the deployment of GDC coils. Examples of such mechanisms are shown and described in U.S. Pat. Nos. 5,578,074, 5,669,905, 5,984,929, and 6,579,308; the entire contents of each being incorporated herein by reference.

In some embodiment specially shaped balloons or the use of two or more balloons can be used to extend ring members or to telescope the side branch assembly 40.

Figure 2:
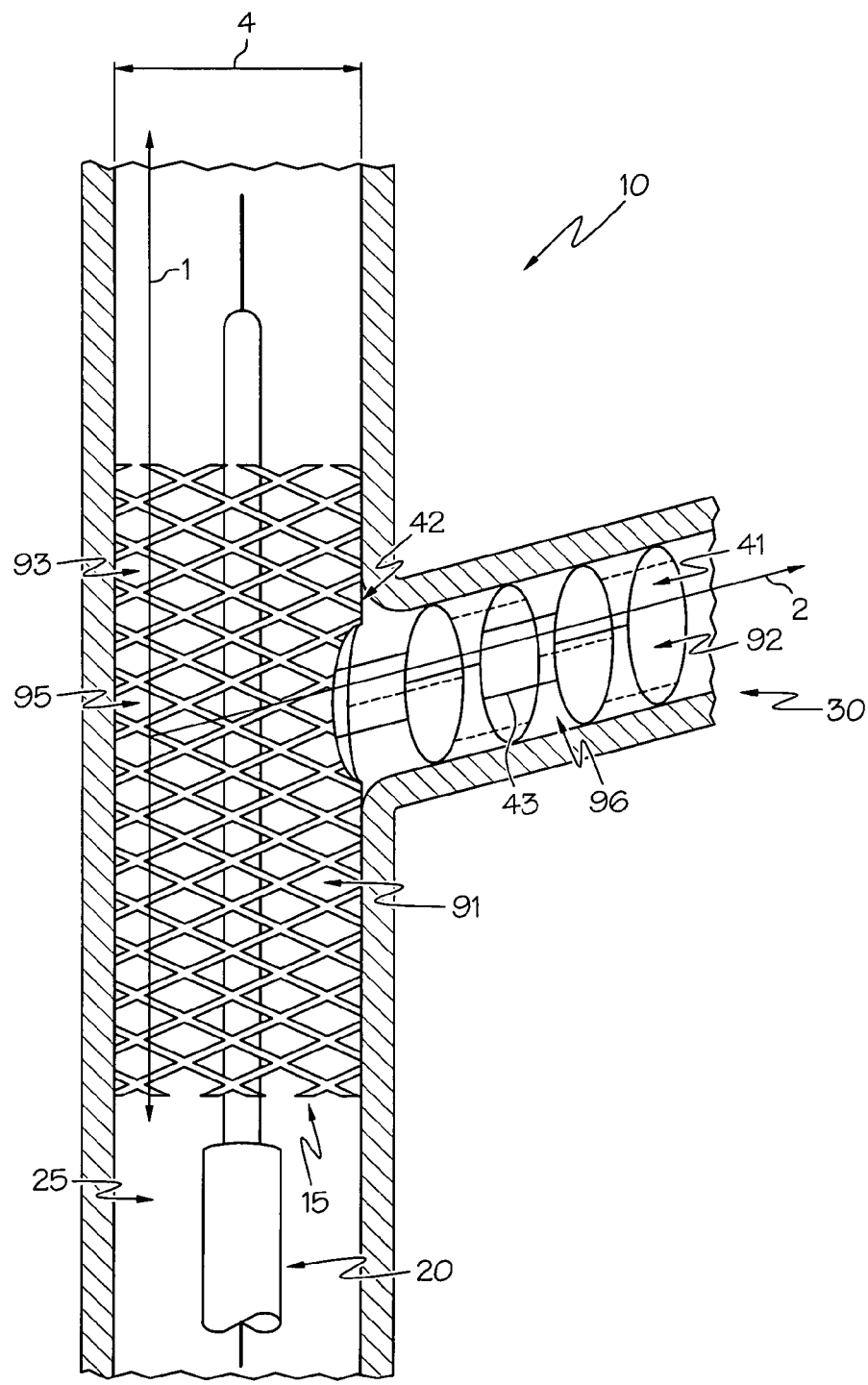
FIG. 2 is an image of an expanded stent containing an extended ring type telescoping bifurcation branch.

Referring now to FIG. 2 there is shown an embodiment of the invention in which the stent 10 is in the expanded state and the ring type side branch assembly 40 is telescoped and is completely deployed. In the deployed state the primary stent body 15 defines a primary lumen 91, has a diameter 4 which is greater than the diameter the stent 10 had in the unexpanded state, and defines a primary circumferential plane, a primary outer surface, and a primary lumen extending about and along the primary longitudinal axis 1. The deployed side branch assembly 40 has at least one telescoped ring member 41 extended into the second vessel lumen 30, and forms a second stent lumen 92 having a second circumferential plane 96 in fluid communication with the primary lumen 91 of the primary stent body 15. This second stent lumen 92 extends about and along a secondary longitudinal axis 2 at an oblique angle to the primary longitudinal axis 1.

This deployment can be accomplished by one or multiple balloons, self expansion, or by any other commonly known mechanism. The side branch assembly 40 can be telescoped before, after, or at substantially the same time that the ring members themselves are extended, and telescoping can occur before, after, or at substantially the same time as the expansion of the primary stent body 10. The ring bifurcation branch can also be telescoped by being fed into the side branch vessel 30 by guide wire 73 (not shown). Once in place, the separate guide wire 73 could have a separate locking mechanism to keep the rings in place. In this illustration all but one of the ring members 41 are extended to a larger circumference than they possessed when untelescoped. As mentioned before, all the ring members 41 need not be of differing circumferences or sizes before telescoping and this invention encompasses devices where any of the ring members 41 are designed to keep constant, increase, or decrease their circumference when telescoped. The side branch assembly 40 projects into the second vessel lumen 30 along a second longitudinal axis 2 which forms an angle with the primary longitudinal axis 1 and can be bent, curved, straight, or posses any number of configurations. The design of the side branch assembly 40 allows for the design of longer side branches branch than can be easily designed with petal type stent configurations.

In this illustration, the ring-ring connectors 43 are longer than they were when the bifurcation branch was untelescoped. This invention contemplates embodiments in which the ring-ring 43 and the ring-stent 42 connectors can also have particular characteristics to facilitate telescoping of the side branch assembly 40. These characteristics include: increasing connector lengths by using one or any combination of commonly known stent connector structures including S shaped connectors, bent connectors, flexible sinusoidal connectors, spring shaped connectors; bending and stretching connectors by constructing them out of flexible or expandable materials, spring shaped connectors, straightening curved connectors; and facilitating connector movement by including pivot mechanisms or engaging the connectors to the ring members or primary stent body by rotating loops or rings. Connector rotation can also facilitate increasing the ring-ring distance.

Figure 3:
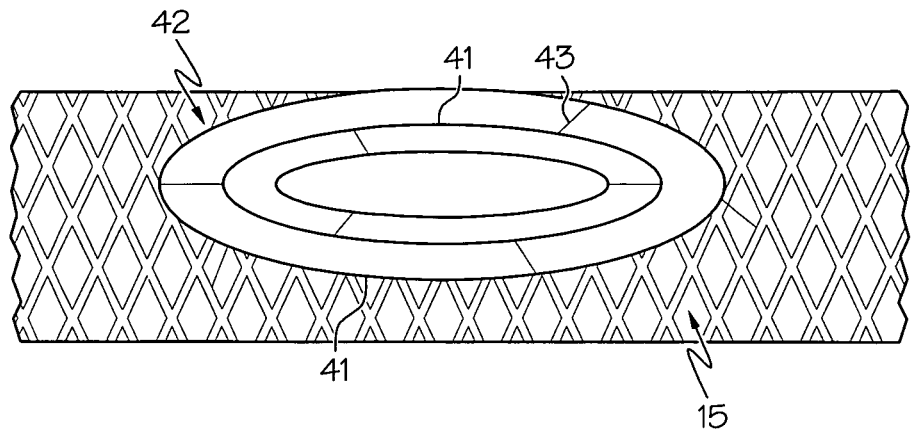
FIG. 3 is a close up view of an unextended ring type telescoping bifurcation branch.
Figure 4:
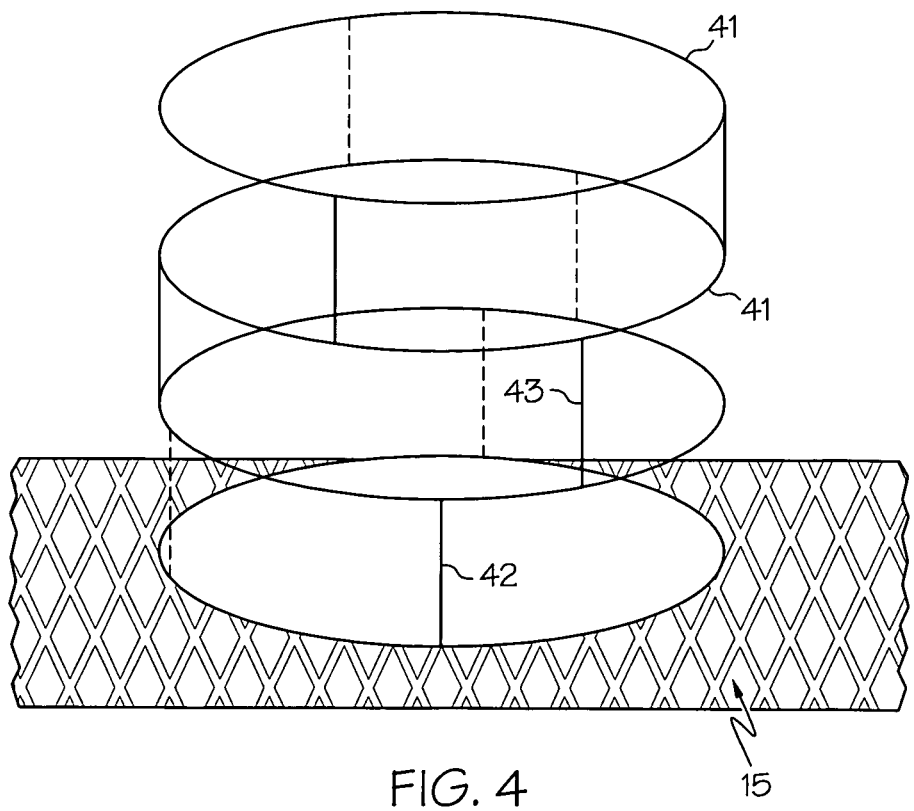
FIG. 4 is a close up view of an extended ring type telescoping bifurcation branch.

Referring now to FIGS. 3 and 4 there are shown close up images of the ring type telescoping side branch assembly 40 made up of ring members 41 attached to the primary stent body 15 by connectors 42. The ring members 41 are also connected to each other by at least one inter-ring connector 43. FIG. 3 features an example of untelescoped ring members and FIG. 4 telescoped ring members.

FIG. 3 includes an untelescoped ring branch assembly 40 in which the unextended ring members 41 are positioned concentrically adjacent to each and within the primary circumferential plane 95. This is only one possible configuration and the ring members 41 can be of uniform size and or be positioned in a non-concentric configurations including laterally adjacent positioning. When the stent 10 is deployed in a body vessel, each ring member can have its circumference extend, contract, or remain constant as the vessel dimensions require. The ring members 41 can be designed to alter their circumference to either a pre-defined circumference or until they are blocked by the vessel walls. The length and shape of connectors 43 or 42 is one way of affecting how far the side branch assembly 40 can extend into the secondary vessel lumen 92. This invention also contemplates secondary lumens 92 having at least partially irregular circumferences and can be tapered (where the circumferences of a series of adjacent ring members 41 gradually and generally change in size).

Figure 5:
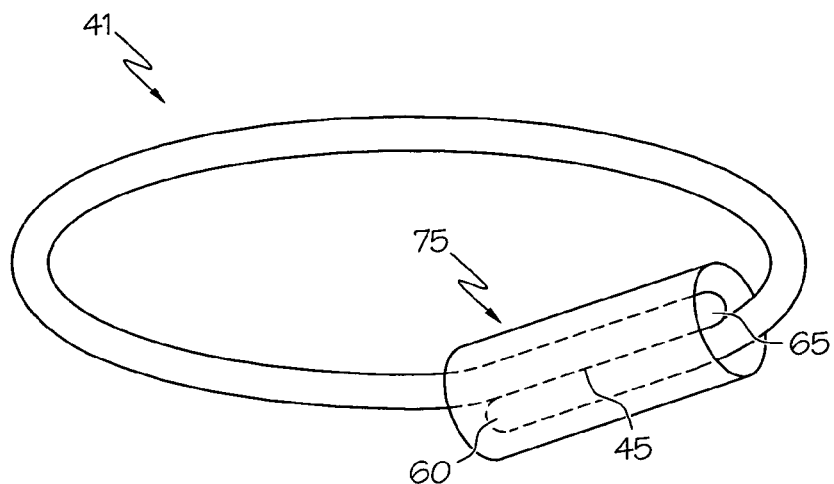
FIG. 5 is an image of a single unextended telescoping ring.

FIG. 5 illustrates an embodiment of an extendable ring member 41 with an overlapping loop configuration. In this embodiment, the ring member 41 has a first ring end 60 and the second ring end 65 adjacent to each other. While unextended, the ring member 41 has an overlap region 45 which reduces the circumference. As the ring member extends, the length of the overlapping region 45 decreases, increasing the circumference. An optional cover 75 can be placed over the overlap region but is not a required component of this embodiment.

Figure 6:
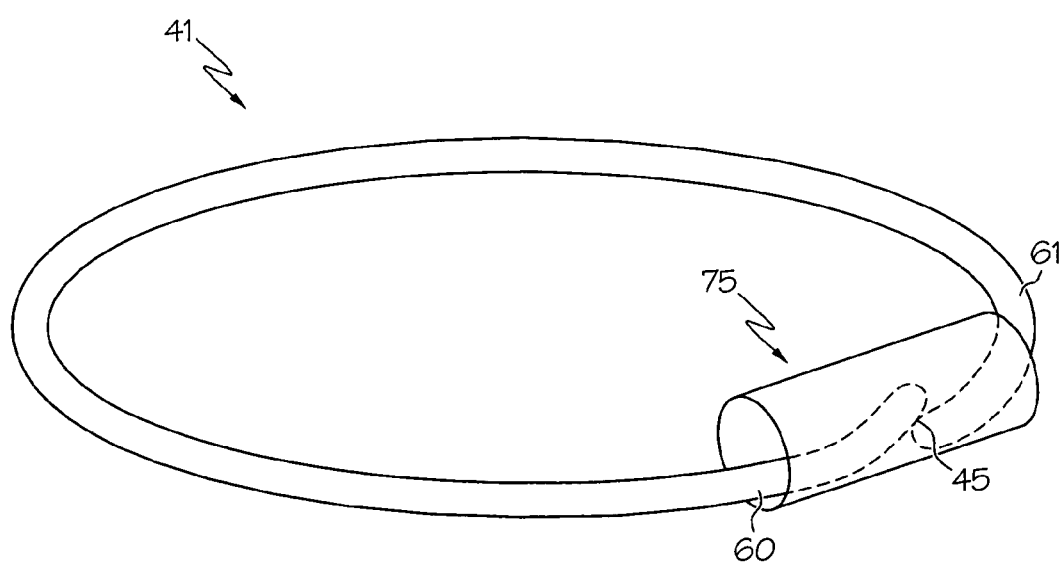
FIG. 6 is an image of a single extended telescoping ring.
Figure 23:
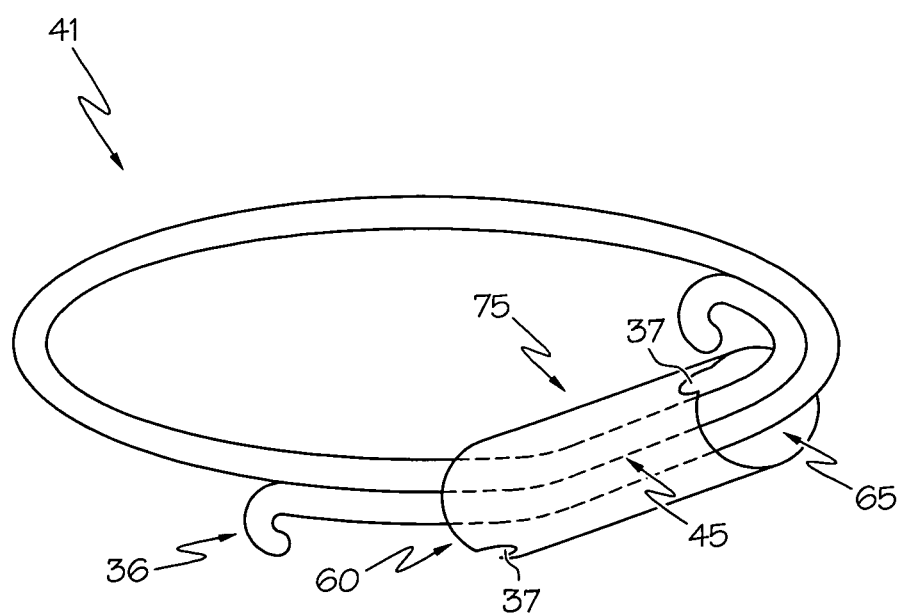
FIG. 23 is an image of a single unextended telescoping ring with wire stops.

FIG. 6 illustrates an embodiment of an extended ring 41 where some of or all of the overlapped portion of FIG. 5 are no longer overlapping thus increasing the ring's circumference. The extent of the circumferential increase caused by the rings expansion can be controlled by the use of wire stops or stopping welds. FIG. 23 illustrates an unexpanded ring in which a wire stop 36 and a stopping weld 37 is added to the ring. As the ring expands and the overlap region 45 decreases, the wire stop 36 moves closer to the opposite ring end (60 or 65). At some point the wire stop 36 becomes caught and stops further ring expansion. In one possible embodiment, the wire stop 36 is stopped when it becomes caught on a stopping weld 37 which can be in the form of a cavity, a hook or other catching region of the cover 75. Although this illustration shows two wire stops on the ends (60, 65) of the rings one or more wire stops can be installed on any region of the ring. In addition, the wire stops can function with or without stopping welds 37 or a cover 75.

Figure 7:
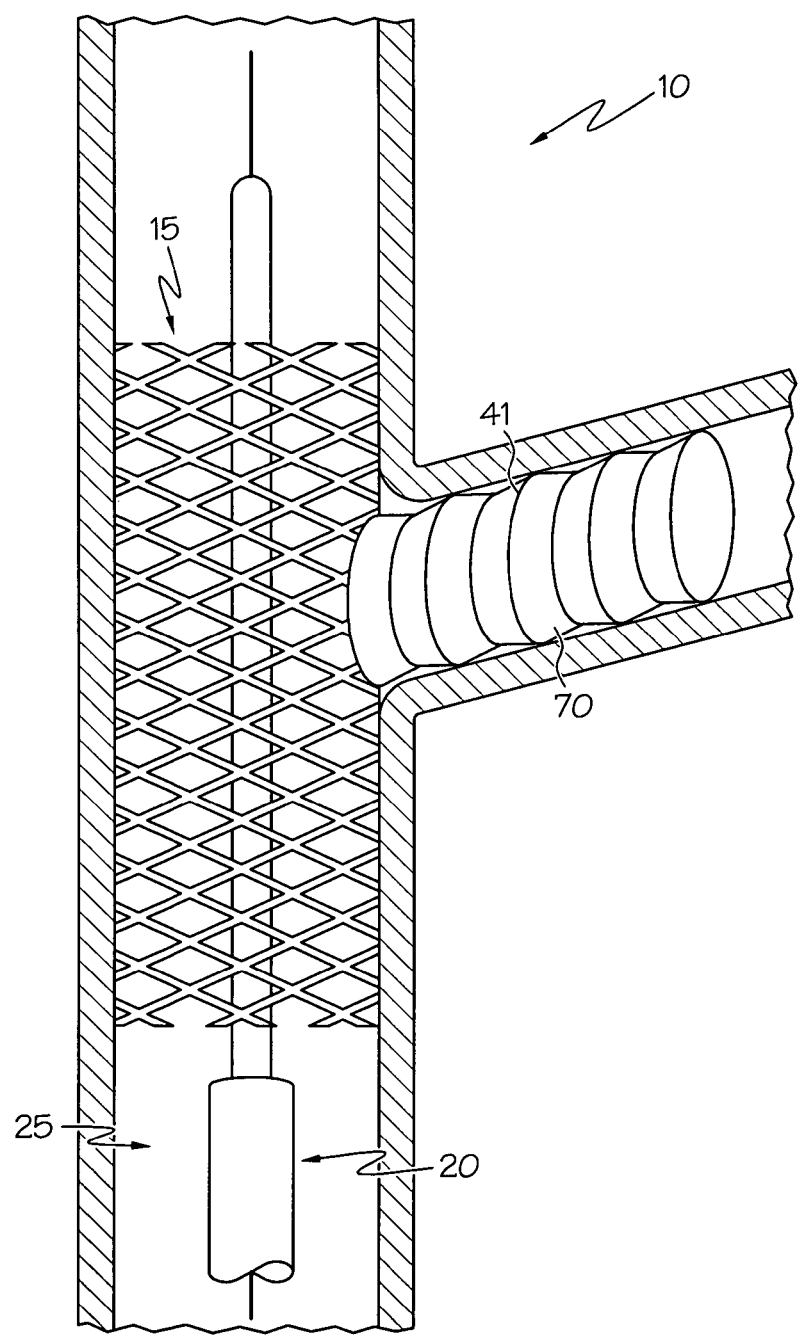
FIG. 7 is an image of an expanded stent containing an extended ring type telescoping bifurcation branch with a PTFE covering.

FIG. 7 illustrates en embodiment of the invention in which the rings 41 of the ring bifurcation branch 40 are engaged to a polymeric sheath 70. This sheath can be constructed out of a number of materials including PTFE (poly(tetrafluoroethylene)) and can be constructed with a variety of flexibility, structural strength, rigidity, and porosity characteristics. The sheath can be positioned within or without the ring members' circumference or the rig members can be an integrated component embedded within at least a portion of the sheath material. This embodiment also contemplates a plurality of sheath layers made up of different materials, having different characteristics, or different positions. The sheath can be designed to fold open as the side branch 40 telescopes during deployment.

There are a number of possible mechanisms that can be used to lock an extended ring member into its final configuration and to assure that the ring member only extends (or contracts) in the desired direction and does not assume an undesired circumference. One of these mechanisms, illustrated in FIGS. 8, 9, 10 and 11 is a ratcheting ring. The ratcheting ring utilizes a locking mechanism used today to fix the circumference of rings locking wires together or sealing waste disposal bags, is commonly referred to as "cable ties", "tie wraps", or "zip ties" and is well known to people of ordinary skill in the art.

Figure 8:
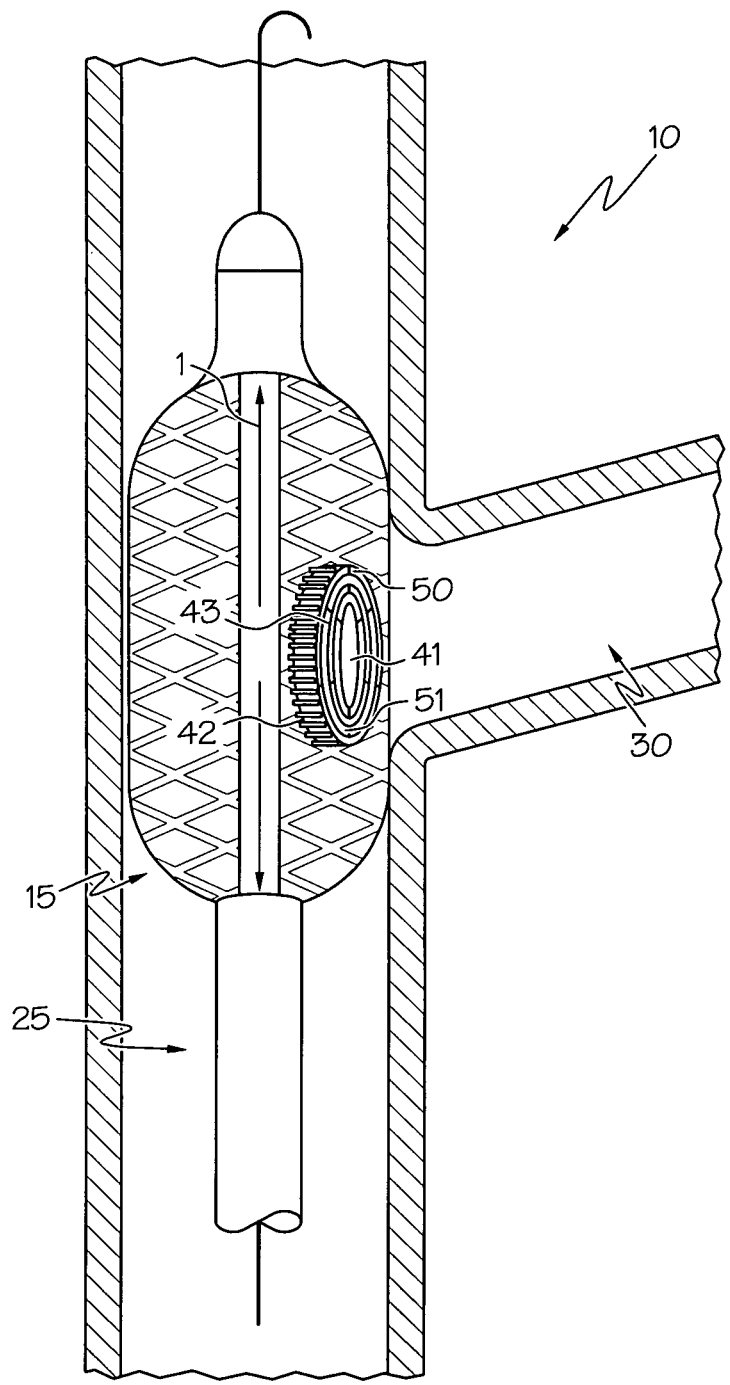
FIG. 8 is an image of an unexpanded stent containing an ratcheting unextended ring type telescoping bifurcation branch.
Figure 9:
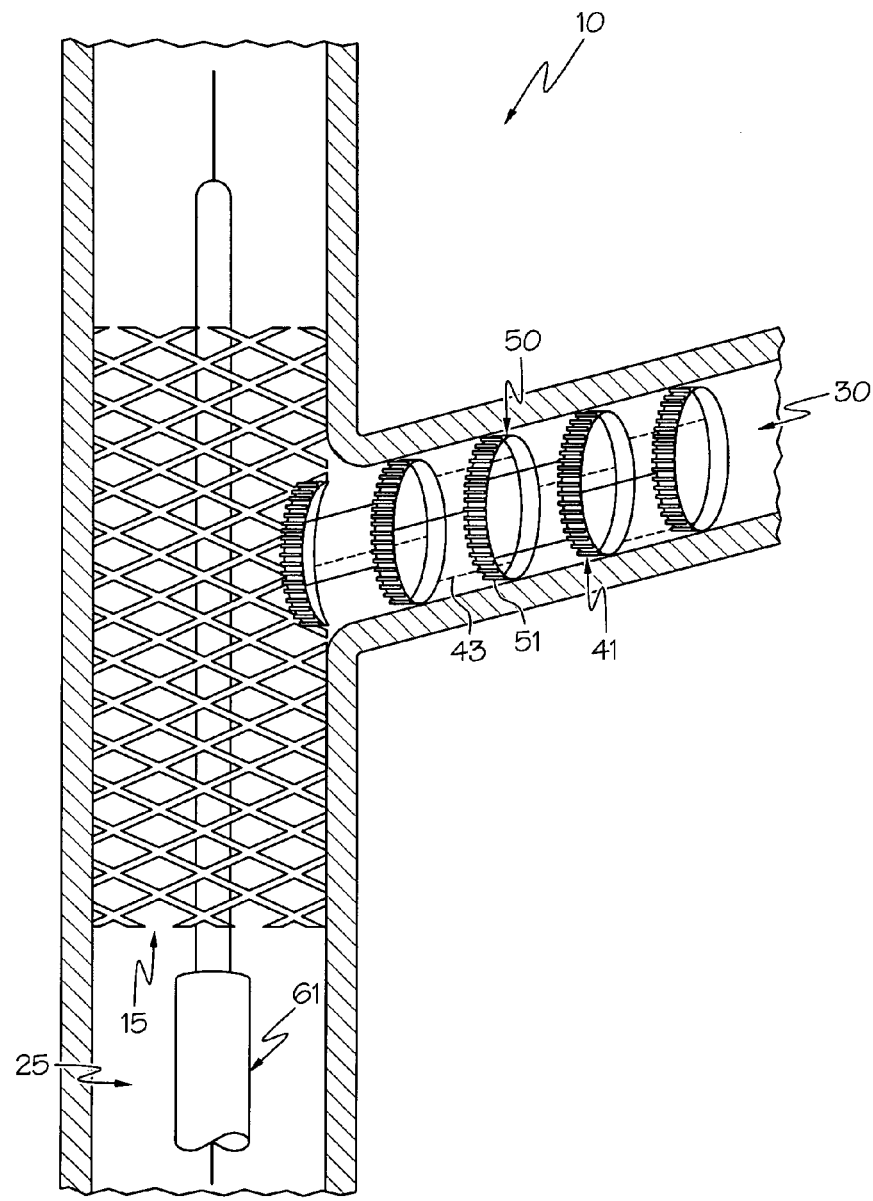
FIG. 9 is an image of an expanded stent containing an extended ratcheting ring type telescoping bifurcation branch.

A side branch assembly 40 with this locking mechanism is illustrated in FIGS. 8 and 9. These figures show ring members 41 with ratchet teeth 50 disposed about at least a portion of the ring member's perimeter and a locking mechanism 51. When extending forces such as balloon pressure or self expansion cause the circumference of the ring member to change, the ratchet teeth 50 are capable of traversing the locking mechanism 51 in one direction but not in another fixing the resulting change in circumference. This mechanism can prevent an increase or a decrease in the size of the ring member 41 circumference. FIG. 8 illustrates unextended ratchet rings attached to an unexpanded stent body 15 and FIG. 9 illustrates extended ratchet rings telescoped into a second vessel body 30.

Figure 10:
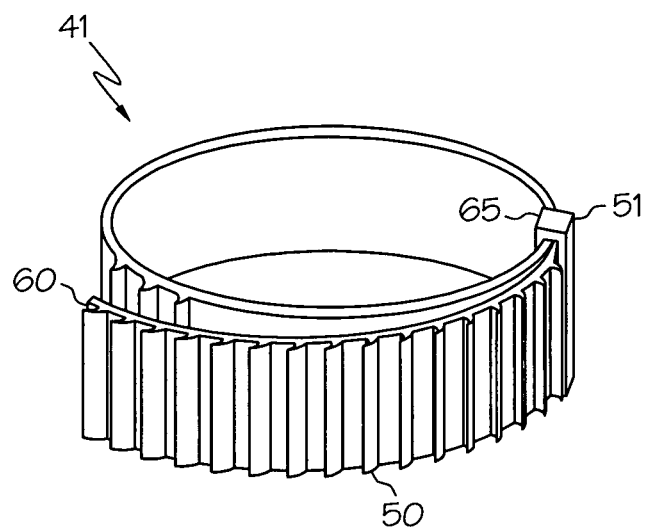
FIG. 10 is an image of a single unextended ratcheting telescoping ring.
Figure 11:
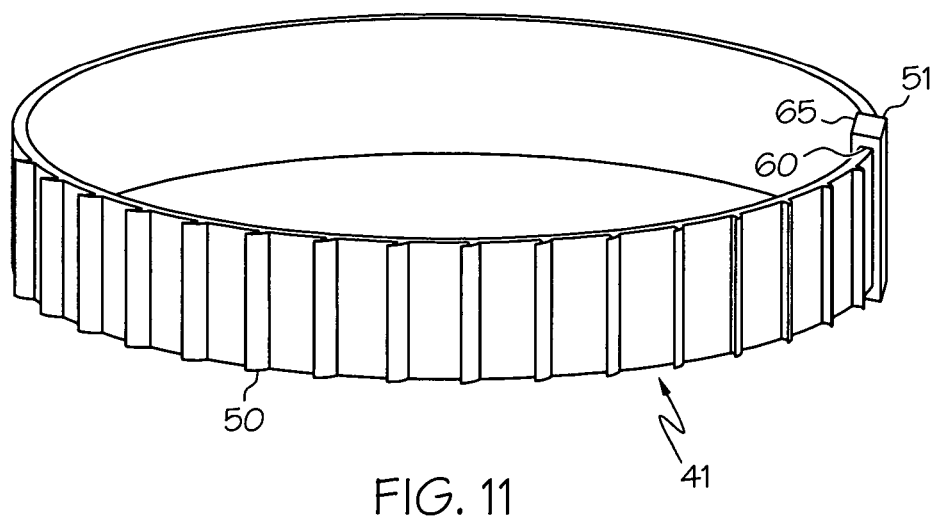
FIG. 11 is an image of a single extended ratcheting telescoping ring.

FIG. 10 illustrates a close up view of a ratchet ring 41. In it a ring member 41 has disposed about its circumference at least one ratchet tooth 50. Ratchet teeth can be triangular, or angled in such a way that locking mechanism 51 can easily rotate about the perimeter in one direction but is blocked from moving in the opposite direction by the tooth/teeth 50. As a result, the ring member 41 can be adjusted to assume a desired circumference and it will not revert back to it original circumference. FIG. 11 illustrates a ratchet ring after it has extended to a larger circumference.

Figure 12:
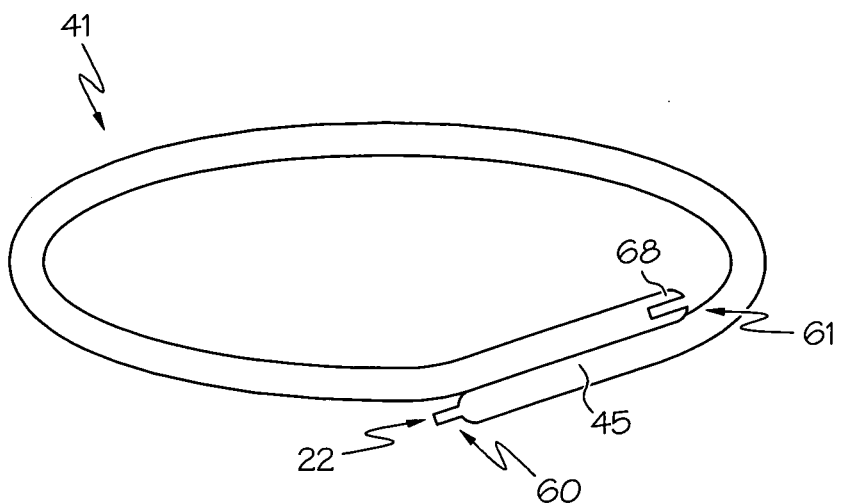
FIG. 12 is an image of a single unextended telescoping ring with a single tongue and groove locking mechanism.
Figure 13:
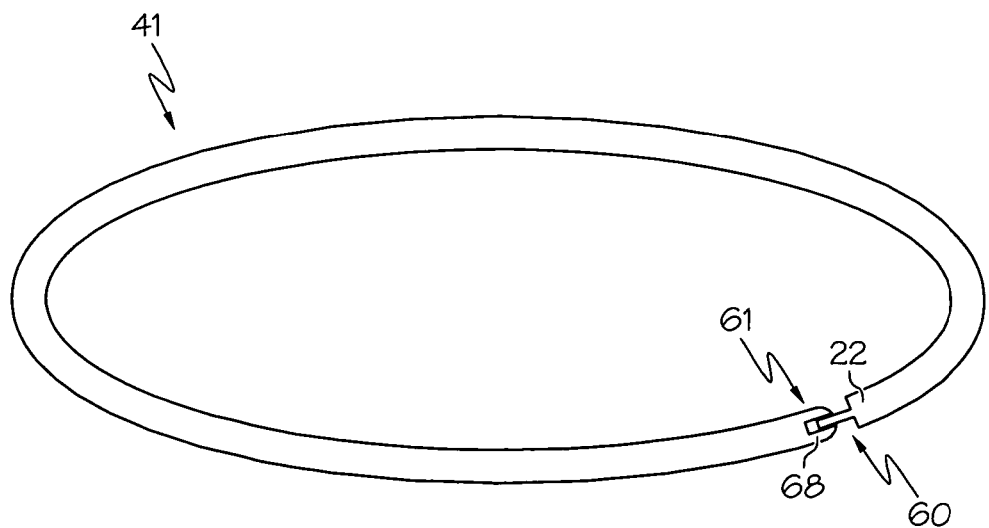
FIG. 13 is an image of a single extended telescoping ring with a single tongue and groove locking mechanism.

Now referring to FIGS. 12 and 13, there is shown an expandable ring member 41 with a single tongue groove locking mechanism. FIG. 12 illustrates the ring member 41 in an unextended state wherein there is an overlap region 45 reducing the ring member's circumference. When this ring member 41 extends as shown in FIG. 13, the locking tongue 22 located on the first end 60 engages the groove 68 located on the ring member's second end 61. In the extended state, by reducing or eliminating the overlap region 45 the ring member's circumference increases. The locking mechanisms 22 and 68, prevent the ring from contracting once the extended circumference has been assumed.

Figure 20:
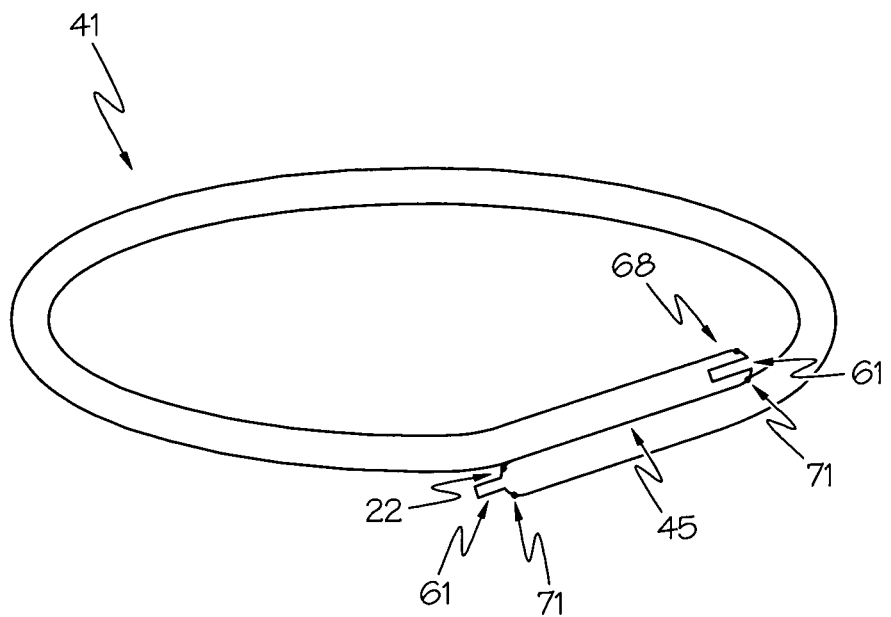
FIG. 20 is an image of the two ends of a single unextended telescoping ring with a single tongue and groove locking mechanism in which a portion of the mechanism has a thrombic material on its surface to glue the ring ends together.
Figure 21:
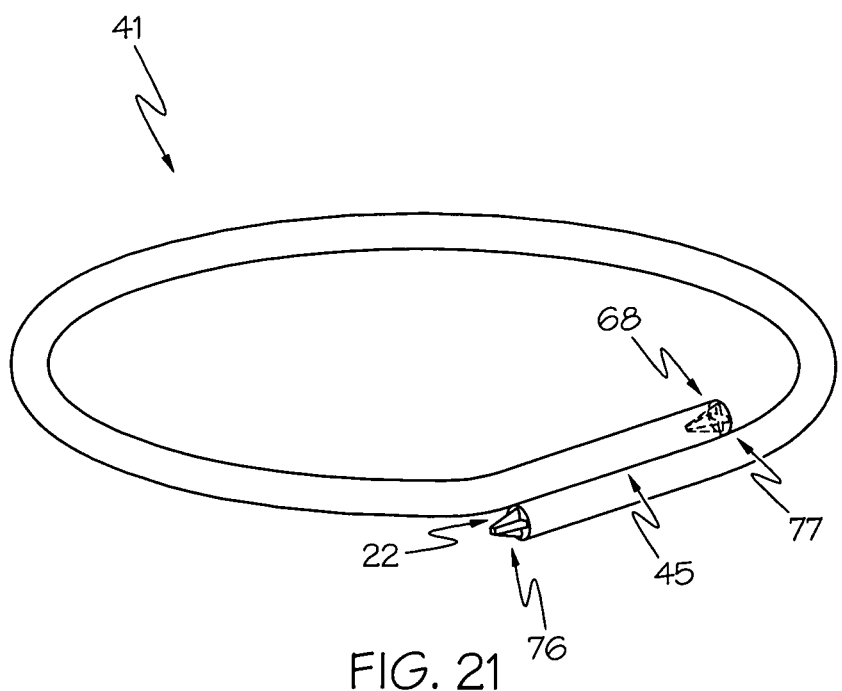
FIG. 21 is an image of the end of the two ends of a single unextended telescoping ring with a "plus" shaped single tongue and groove locking mechanism.
Figure 22:
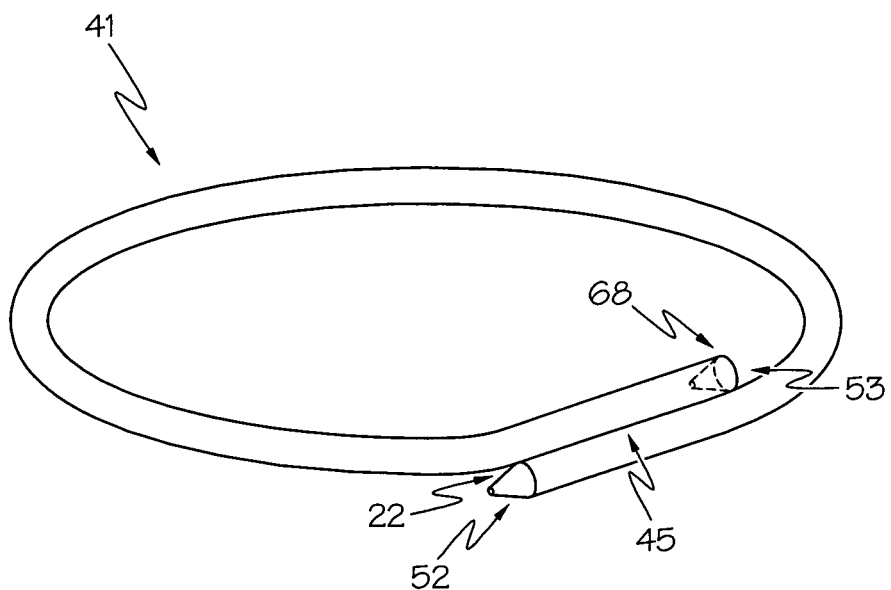
FIG. 22 is an image of the end of the two ends of a single unextended telescoping ring with a conical shaped single tongue and groove locking mechanism.

There are a number of additional possible embodiments of the expandable ring member 41 with a single tongue groove locking mechanism. In one possible embodiment (as illustrated in FIG. 20), at least a portion of the locking mechanism has an adhesive or thrombogenic material 71 on its surface capable of at least partially binding the interlocked ends 60, 61 of the ring together. Although FIG. 20 illustrates the thrombogenic materials on specific regions of both ring ends, this embodiment encompasses thrombogenic materials on any region of either or both ring ends. In a second possible embodiment (as illustrated in FIG. 21), the locking mechanism 22 comprises a pin with a plus shaped extension 76 which fits into and engages a grove 68 with a plus shaped socket 77. In a third possible embodiment (as illustrated in FIG. 22), the locking mechanism 22 comprises a pin with a conical shaped extension 52 which fits into and engages a grove 68 with a cone shaped socket 53.

Figure 14:
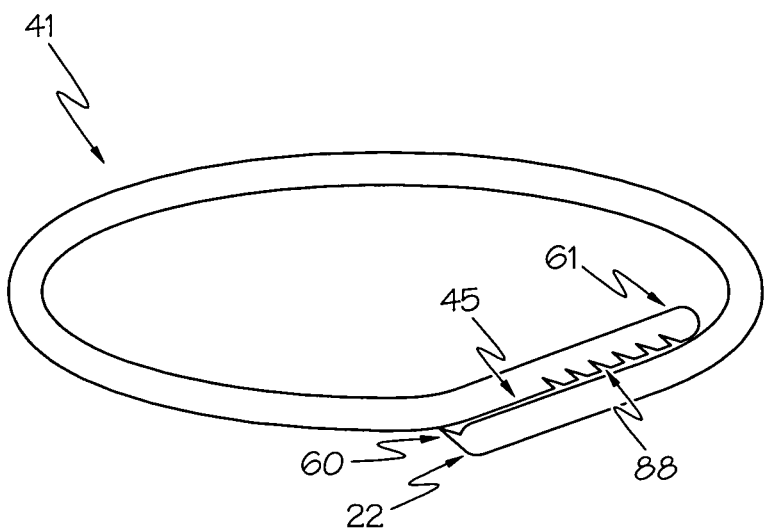
FIG. 14 is an image of a single unextended telescoping ring with a multiple tongue and groove locking mechanism.
Figure 15:
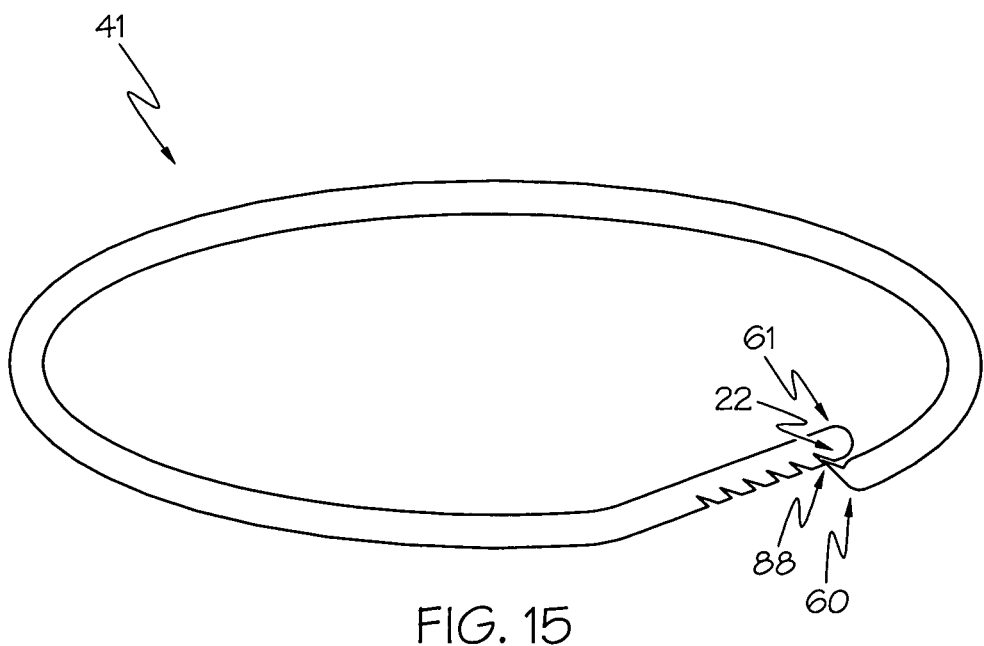
FIG. 15 is an image of a single extended telescoping ring with a multiple tongue and groove locking mechanism.

Now referring to FIGS. 14 and 15, there is shown an expandable ring with a multiple tongue groove locking mechanism. FIG. 14 illustrates the ring 41 in an unextended state wherein there is an overlap region 45 reducing the ring's circumference. When this ring extends as shown in FIG. 15, the locking tongue 22 located on the first end 60 engages the grooves 88. These groves allow for a number of possible extended states with a reduced or eliminated overlap region 45. The locking mechanisms 22 and 88 prevent the ring from contracting once the desired extended circumference has been assumed.

Figure 16:
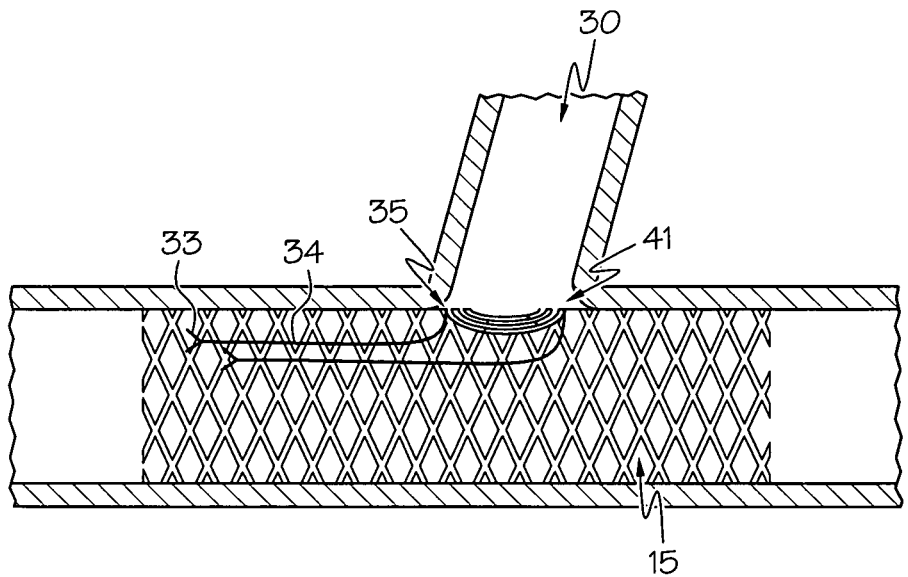
FIG. 16 is an image of the stent with added unengaged support structure.
Figure 17:
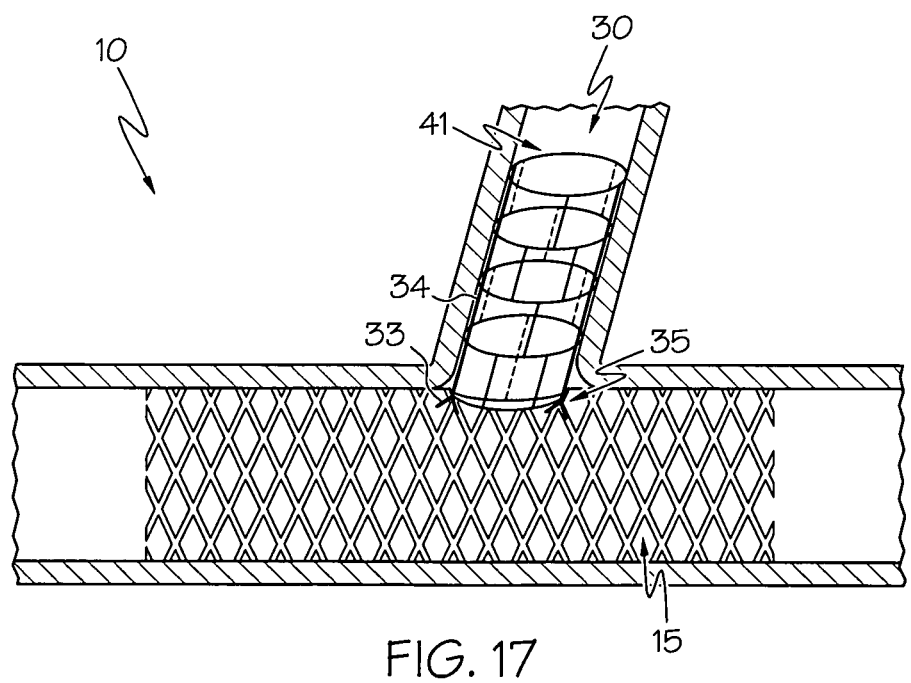
FIG. 17 is an image of the stent with added engaged support structure.

Referring now to FIGS. 16 and 17 are an embodiment of the stent in which there is added at least one structural support 34 with a support locking mechanism 33. The support locking mechanism 33 can be a hook located at the end of the structural support 34 or can be located at any position along the length of the structural support 34. The structural support 34 can be a wire or any flexible or curved material. In FIG. 16 the ring side branch assembly 40 has not yet telescoped so the structural support 55 has not yet engaged with the locking position 35 on the stent main body 15. In FIG. 17 at least one ring member 41 has been telescoped and the locking mechanism 33 has engaged the locking position 35. This structural support 34 can be used to both telescope the ring members 41 by pushing them out into the second vessel lumen 30 or they can be used to provide additional support connecting the side branch assembly 40 to the stent main body 10. In addition the support structure can replace the stent-ring or ring-ring connectors.

Figure 18:
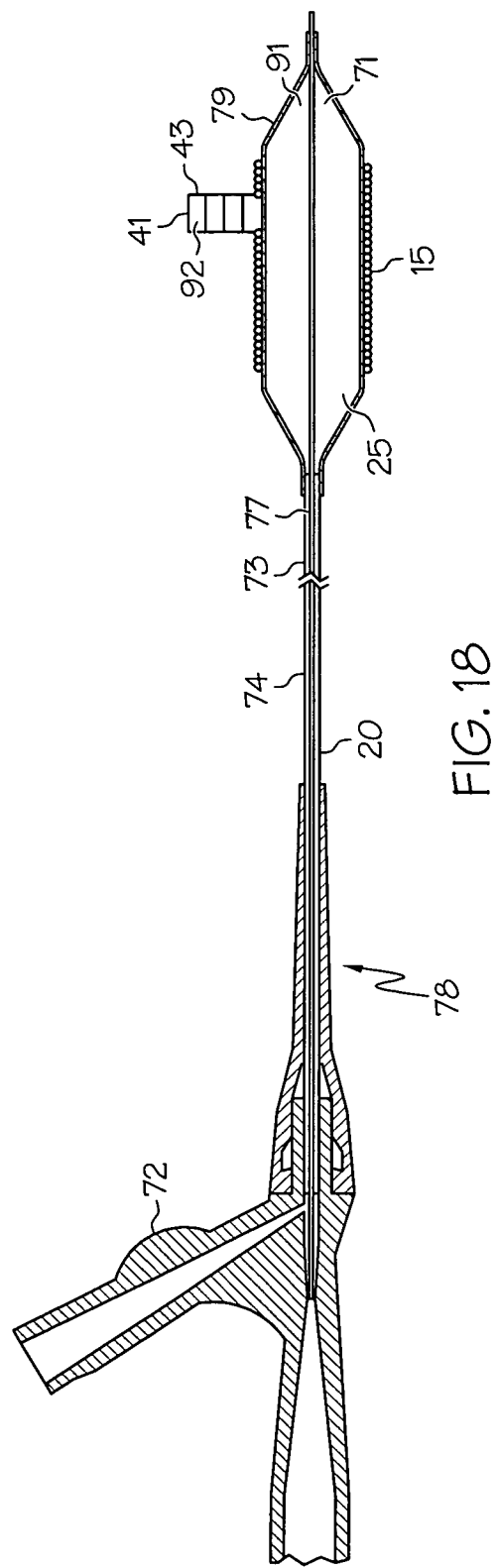
FIG. 18 is an image of a stent delivery system with the expanded stent upon a catheter.

Referring now to FIG. 18 there is shown a longitudinal cross-sectional view of an example of a stent delivery system 78 capable of delivering a bifurcated stent 10 with a side branch assembly having at least one ring member 41 and at least one ring-ring and/or ring-stent connector 43 to form a second fluid lumen 30. The stent delivery system 78 includes a stent 10 disposed around the distal end of a catheter shaft 20. The distal end of the catheter shaft 20 is inserted through the first vessel lumen 25 of the main stent body 20. In this illustration the stent delivery system 78 is representative of a simple over-the-wire (OTW) or single-operator-exchange (SOE) angioplasty balloon catheter according to the invention. Such balloon catheters are discussed, for example, in commonly assigned U.S. Pat. Nos. 6,113,579, 6,517,515 and 6,514,228, each of which is incorporated by reference herein in its entirety. In this embodiment, the system also features a conventional OTW-type manifold assembly 72 connected to proximal end of catheter shaft assembly 20. The catheter shaft assembly 20 includes an outer tube 74 coaxially disposed about inner tube 73 which defines a guide wire lumen 77 and a distal end about which is disposed balloon 79. During deployment, the balloon 79 is inflated, thus expanding the stent at the lesion site. This is only an illustration of such a catheter assembly and is not intended to limit the scope of the present invention. This invention also encompasses stent delivery systems which do not contain a balloon expanding attributes such as self expanding stents or fixed wire systems. Numerous structures are known to those of skill in the art, any of which may be employed herein.

In some embodiments the stent, its delivery system, or other portion of an assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque. In some embodiments the delivery system of the side deployment mechanism includes balloon inflation, self expansion, and guide wire pushing or pulling.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A bifurcated stent being expandable from an unexpanded state to an expanded state, wherein in the unexpanded state the stent has a diameter less than that of the diameter in the expanded state, the bifurcated stent comprising:
   a substantially tubular primary body defining a primary circumferential plane, a primary outer surface, a primary lumen and having a primary longitudinal axis extending therethrough;
   a side branch assembly engaged to the primary body, the side branch assembly comprising a plurality of ring members, adjacent ring members being engaged one to the other by at least one connector, in the unexpanded state the plurality of ring members being positioned substantially within the primary circumferential plane, in the expanded state the plurality of ring members being positioned external to the primary circumferential plane and defining a secondary lumen, and having a secondary longitudinal axis extending therethrough, the secondary lumen being in fluid communication with the primary lumen, the secondary longitudinal axis forming an angle with the primary longitudinal axis,
   wherein the plurality of ring members are generally circular, and
   wherein the ring members have an unexpanded circumference in the unexpanded state and at least two of the plurality of ring members have substantially the same unexpanded circumference.

2. The stent of claim 1 wherein the ring members have an expanded circumference in the expanded state, wherein the expanded circumference is greater than the unexpanded circumference.

3. The stent of claim 2 wherein the ring members are constructed and arranged to self expand from the unexpanded circumference to the expanded circumference.

4. The stent of claim 2 wherein the ring members are engaged to the primary body by at least one engagement region, the at least one engagement region having an engaged state and a released state, in the engaged state the at least one ring member being retained in the unexpanded state and in the released state the at least one ring member being released to expand to the expanded state.

5. The stent of claim 1 wherein the at least one connector has a first end, a second end and a length therebetween, each end being flexibly engaged to one of the rings.

6. The stent of claim 1 wherein the at least one of the expanded state and the unexpanded state of at least two ring members have differing circumferences.

7. The stent of claim 1 wherein the secondary lumen comprises a length and a diameter, the diameter tapering along at least a portion of the length.

8. A bifurcated stent being expandable from an unexpanded state to an expanded state, wherein in the unexpanded state the stent has a diameter less than that of the diameter in the expanded state, the bifurcated stent comprising:
   a substantially tubular primary body defining a primary circumferential plane, a primary outer surface, a primary lumen and having a primary longitudinal axis extending therethrough;
   a side branch assembly engaged to the primary body, the side branch assembly comprising a plurality of ring members, adjacent ring members being engaged one to the other by at least one connector, in the unexpanded state the plurality of ring members being positioned substantially within the primary circumferential plane, in the expanded state the plurality of ring members being positioned external to the primary circumferential plane and defining a secondary lumen, and having a secondary longitudinal axis extending therethrough, the secondary lumen being in fluid communication with the primary lumen, the secondary longitudinal axis forming an angle with the primary longitudinal axis,
   wherein the ring members have an unexpanded circumference in the unexpanded state and at least two of the plurality of ring members have substantially the same unexpanded circumference.

9. The stent of claim 8, wherein the connectors are substantially straight in both the unexpanded state and the expanded state.

10. The stent of claim 8, wherein the at least one of the expanded state and the unexpanded state of at least two ring members have differing circumferences.

11. The stent of claim 8, wherein in the unexpanded state the plurality of ring members are concentrically arranged relative to one another.

* * * * *